United States Patent [19]

Omatsu et al.

[11] Patent Number: 4,935,488
[45] Date of Patent: Jun. 19, 1990

[54] TRIMETHYLOLHEPTANES AND USE THEREOF

[75] Inventors: Toshihiro Omatsu; Yasuo Tokitoh; Noriaki Yoshimura; Masao Ishida; Makoto Yano; Koji Hirai, all of Kurashiki; Yoichi Matsumoto, Kamisu; Keiji Kubo, Kurashiki, all of Japan

[73] Assignee: Kurary Company, Ltd., Kurashiki, Japan

[21] Appl. No.: 340,791

[22] Filed: Apr. 20, 1989

[30] Foreign Application Priority Data

| Apr. 20, 1988 | [JP] | Japan | 63-99115 |
| May 24, 1988 | [JP] | Japan | 63-127678 |
| Jan. 20, 1989 | [JP] | Japan | 64-12666 |
| Jan. 20, 1989 | [JP] | Japan | 64-12667 |

[51] Int. Cl.$^5$ .................................. C08G 63/02
[52] U.S. Cl. ............................ 528/272; 528/295.5; 528/296; 528/302; 528/304; 528/308.6; 528/392; 528/396; 525/437; 525/440; 525/445; 525/447; 525/451; 560/190; 560/201; 560/204; 568/853

[58] Field of Search .............. 528/272, 295.5, 296, 528/302, 304, 308.6, 392, 396; 525/437, 440, 445, 447, 451; 560/190, 201, 204; 568/853

[56] References Cited

U.S. PATENT DOCUMENTS

| 3,900,686 | 8/1975 | Ammons et al. | 428/425 |
| 3,965,057 | 6/1976 | Ammons et al. | 528/339 |
| 4,101,529 | 7/1978 | Ammons | 528/67 |
| 4,121,014 | 10/1978 | Shaffer | 428/412 |
| 4,361,692 | 11/1982 | Ammons | 528/51 |
| 4,434,284 | 2/1984 | Rukavina et al. | 528/58 |
| 4,594,402 | 6/1986 | Coleman et al. | 528/49 |

Primary Examiner—John Kight, III
Assistant Examiner—S. A. Acquah
Attorney, Agent, or Firm—Oblon, Spivak, McClelland, Maier & Neustadt

[57] ABSTRACT

Novel trimethylolheptanes having three highly reactive hydroxyl groups are provided. They are useful as raw materials for the production of polyesters for use in or as raw materials or modifiers for paints, inks, adhesives, coating compositions and molding resins. Uses for the trimethylolheptanes are also provided.

31 Claims, 5 Drawing Sheets

TRIMETHYLOLHEPTANES AND USE THEREOF

BACKGROUND OF THE INVENTION

1. Field of the Invention

This invention relates to trimethylolheptanes and use thereof.

2. Description of Prior Arts

Among the known trimethylolalkanes, there are 1,1,1-trimethylolalkanes, such as 1,1,1-trimethylolethane and 1,1,1-trimethylolpropane. These 1,1,1-trimethylolalkanes are used as raw materials for the production of alkyd resins, polyurethane resins and so forth. It is also known that 1,1,1-trimethylolheptane is useful as a raw material for the production of polyesters, polyurethanes and so on (Japanese Laid-open Patent Application Kokai No. 148134/1986).

When the above-mentioned 1,1,1-trimethylolalkanes, for example 1,1,1-trimethylolethane and 1,1,1-trimethylolpropane, are used as raw materials for the production of alkyd resins, polyurethane resins and so on, the three hydroxyl groups of each 1,1,1-trimethylolalkane are utilized for the formation of bonds with the functional groups of other molecular species, for example an ester bond, a urethane bond, etc. However, the three methylol groups of a 1,1,1-trimethylolalkane are bound to one and the same carbon atom and, therefore, the steric hindrance among the three hydroxyl groups is relatively high, so that the three hydroxyl groups each do not always show sufficiently high reactivity. In particular, when two of the three hydroxyl groups of a 1,1,1-trimethylolalkane each form a bond as a result of reaction with some other molecule, the remaining third hydroxyl group has considerably reduced reactivity, so that resins produced by using a 1,1,1-trimethylolalkane require a fairly long time for curing or hardening. Accordingly, one can hardly say that 1,1,1-trimethylolalkanes always have properties satisfactory for their use as raw materials in the production of resins, among others.

Polyester resins obtained by esterification of a polybasic acid and a polyhydric alcohol are in wide use in the form of fibers and also in the form of films, molding materials, coating compositions and so on. In particular, polyester resins are widely used in household paints and paints for use in building industry and other industries, among others, and are one of the most important classes of paint resins since they have luster and since, in addition, their paint characteristics can be varied fairly optionally by varying the starting material polybasic acid and/or polyhydric alcohol, the quantity ratio therebetween, the molecular weight, acid value or hydroxyl value of the resin and the quantity ratio between the resin and the curing agent, among others.

Automobile paints, for example, are required to have good chipping resistance in many instances. Precoated metal sheets are required to have good flexing resistance, and paint films applied to plastics to be resistant to cracking and breaking due to deformation of paint film-bearing plastics. Thus, there is a field in which polyester resin paints are required to have flexing resistance and flexibility.

Polyester resin-based paints have good flexing resistance by nature. As possible means of giving flexibility to polyester resins, there may be mentioned, among others, making to react with long-chain fatty acids, reducing the degree of crosslinking, or using long-chain aliphatic polybasic acids and polyhydric alcohols while reducing the quantity of aromatic acids. In actuality, however, such means cause decreases in paint film hardness, strength and/or durability and in compatibility with other resins or curing agents (hardeners). For these and other drawbacks, said means of giving flexibility each has its limit. There is a great demand for means of giving flexibility to polyester resins without impairing the above-mentioned properties, in particular hardness.

The so-called high-solid paints which contain solids in increased concentrations and solvents in decreased contents are advantageous from the energy saving and pollution control viewpoints and are in much increased demand nowadays. High-solid compositions may be obtained by using resins which do not cause any significant or excessive increase in solution viscosity even when the resin concentration is increased. Reduction in resin molecular weight is effective in preparing high-solid compositions but at the same time results in decreases in paint film characteristics in many instances. For preparing high-solid compositions, it is therefore important to have a low-viscosity resin without decreasing the molecular weight.

Curability is also an important performance characteristic of paints. Generally, paint films can have desired physical properties only after paint gelation by three-dimensional crosslinking. While unsaturated polyester resins can be cured by crosslinking reaction of double bonds, for instance, contained in themselves, curing is attained in many instances by reaction of a curing agent, such as an amino resin (aminoplast) or a polyisocyanate, with the terminal hydroxyl (—OH) groups of polyester resins. If the rate of the reaction between polyester resin hydroxyl groups and such a curing agent is slow, a long period of time is required for curing (in general terms, drying of paint). If the curing temperature is raised to promote curing, resins may be discolored or decomposed. If the rate of curing reaction is excessively fast, the curing reaction may proceed already before paint application following admixture of a curing agent with polyester resins. In such case, the paints obtained may gelate or acquire an increased solution viscosity before application, decreasing the stability of the paints. It is desirable that the curing of paint resins will not take place during storage but can proceed in the step of drying or baking as rapidly and uniformly as possible. If this curing reaction is not complete, unreacted functional groups react gradually over a long period after film formation, inducing changes in physical properties of coat films with the lapse of time. When polyhydric alcohols so far in use as branching agents for polyesters, for example glycerin, trimethylolpropane, pentaerythritol, etc., are used, the rate of curing reaction becomes slow and the curing reaction will not be complete.

In recent years, the so-called radiation-curable resin compositions capable of being cured by irradiation with ultraviolet rays, electron beams or the like have come into practical use in various paints, coating compositions, inks, printing materials, adhesives, resists, insulating varnishes, optical fibers and so on. They have rapid curability and are solvent-free and, therefore, are advantageous from the resources saving, energy saving, pollution control and high productivity viewpoints as compared with thermosetting resins. Generally, however, the radiation-curable resin compositions, which have the above-mentioned advantages, still have problems to be solved particularly with respect to toxic properties of polyfunctional polymerizable monomers (also called reactive diluents) to be used therein or to pliability, toughness and adhesion of coat films obtained after polymerization. This is one material reason why the production of such resins have not attained rapid growth contrary to expectation.

Accordingly, the advent of radiation-curable resin compositions rich in flexibility, toughness and adhesion but low in toxicity is earnestly waited for.

Meanwhile, trimethylolpropane tri(meth)acrylate is used as a polyfunctional polymerizable monomer in a very wide range and in large quantities.

However, trimethylolpropane triacrylate has a primary skin irritation index (P.I.I.) of 4.8, namely high skin irritating property. Therefore, it is necessary in handling it to use care to avoid skin contact and to prevent hazard in case of skin contact to the utmost. Furthermore, when said trimethylolpropane tri(meth)acrylate is added in large amounts, the toughness, flexibility and adhesion of coat films are much decreased.

In recent years, various fields where tough coat films having high strength and elongation or coat films having flexibility and pliability are earnestly desired have been expanding rapidly. Fields in which cured coat films are required to have satisfactory durability and low-temperature resistance also have been expanding. It is also important that a polyfunctional polymerizable monomer should have good diluting effect, good workability and good applicability.

Generally, the skin irritation mentioned above can be reduced by increasing the molecular weight of the polymerizable monomer. However, an increased molecular weight brings about an increased viscosity, whereby the diluting effect is reduced. Furthermore, the increase in molecular weight means a decrease in (meth)acryl group density; the curability and weather resistance are markedly decreased. It has thus been difficult to meet these contradictory requirements simultaneously.

Accordingly, it is an object of the invention to provide novel trimethylolalkanes having three highly reactive hydroxyl groups.

Another object of the invention is to provide certain uses of said trimethylolalkanes.

A third object of the invention is to provide, as a use of said trimethylolalkanes, polyester resins having a low glass transition temperature and rich in flexibility and low-temperature resistance.

A fourth object of the invention is to provide polyester resins with which high solid paints can be prepared and which have a low viscosity as compared with other resins comparable thereto in molecular weight.

A fifth object of the invention is to provide resins which can be brought to complete cure with ease and at a high curing rate.

A further object of the invention is to provide, as a use of said trimethylolalkanes, polymerizable monomers having a low viscosity, good dilution effect, low skin irritation, low toxicity and good curability.

A still further object of the invention is to provide radiation-curable resin compositions containing said polymerizable monomers and having good workability and good curability as well as tough coat films which are obtainable by curing said resin compositions and have good durability and low temperature resistance.

These objects as well as other objects and advantages of the present invention will become apparent to those skilled in the art from the following detailed description.

SUMMARY OF THE INVENTION

In one aspect, the invention provides a trimethylolheptane selected from the group consisting of 1,1,7-trimethylolheptane, 1,1,6-trimethylolheptane and 1,6,6-trimethylolheptane.

In another aspect, the invention provides a polyester consisting of a polybasic acid component and a polyhydric alcohol component, characterized in that said polyhydric alcohol component is composed of 0.5 mole percent to 100 mole percent of a trimethylolheptane characterized by terminal primary alcohol groups with one hydroxyl group being separated from at least one other hydroxyl group by a carbon chain containing at least 8 carbon atoms, or an ester-forming derivative thereof, and 99.5 mole percent to 0 mole percent of at least one other polyhydric alcohol or an ester-forming derivative thereof, at least 50 percent of the terminal functional groups of said polyester being the hydroxyl group.

In its third aspect, the invention provides a coating resin composition characterized by containing 60 to 95 percent by weight, on the vehicle basis, of said polyester and 5 to 40 percent by weight, on the same basis, of an aminoplast or a polyisocyanate as well as a coat film produced by curing of said coating resin composition.

In a further aspect, the invention provides trimethylolheptane triacrylates or trimethacrylates [hereinafter referred to as "trimethylolheptane tri(meth) acrylates"] and a method of producing the same.

In a still further aspect, the invention provides a resin composition which contains a trimethylolheptane triacrylate or trimethacrylate [hereinafter referred to as "trimethylolheptane tri(meth)acrylate"] as well as a coat film produced by curing of said resin composition.

DETAILED DESCRIPTION OF THE INVENTION

Figure 1:
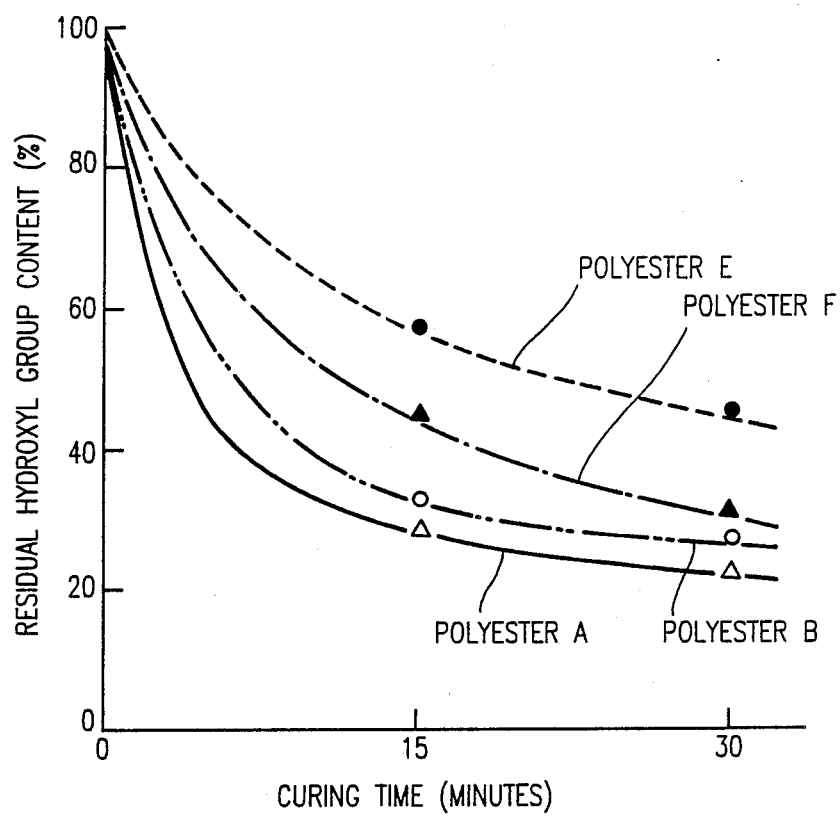
FIG. 1 graphically shows the rates of curing of the polyester paints prepared from the resins respectively obtained in Example 4, Example 5, Comparative Example 1 and Comparative Example 2.

The 1,1,7-trimethylolheptane according to the invention can be produced by a process comprising hydroformylating octa-2,7-dien-1-ol and hydrogenating the hydroformylation product (hereinafter, this process is referred to as "process A"), by a process comprising reacting 1,9-nonanedial with formaldehyde in the presence of a base and hydrogenating the product (hereinafter, this process is referred to as "process B"), or by some other process. The processes A and B are described below in more detail.

Process A

The hydroformylation of octa-2,7-dien-1-ol is effected by reacting octa-2,7-dien-1-ol with hydrogen and carbon monoxide in the presence of a hydroformylation catalyst. The hydroformylation catalyst may be any of those hydroformylation catalysts generally used in the hydroformylation of olefinic compounds, such as rhodium catalysts, cobalt catalysts and ruthenium catalysts. From the high reaction yield viewpoint, however, rhodium catalysts are preferred. Usable as the rhodium catalysts are, for example, rhodium complexes, such as rhodium carbonyl and dicarbonylacetylacetonatorhodium, and rhodium compounds, such as rhodium acetate, rhodium chloride and rhodium oxide. These rhodium complexes, rhodium compouds and so forth may be used in a ligand-modified form. As the ligand, there may be mentioned, among others, phosphines, such as triphenylphosphine and tricyclohexylphosphine, and phosphites, such as triphenyl phosphite and tris(o-t-butylphenyl) phosphite. Preferred as the rhodium catalysts are rhodium catalysts modified with a phosphite, such as tris(o-t-butylphenyl) phosphite, since they can promote 1,1,7-trimethylolheptane precursor formation at a high reaction rate at a low catalyst concentration. Generally, the rhodium catalysts are used in a concentration, on the rhodium atom basis, of 0.005 to 5 milligram atoms per liter (reaction mixture). The hydroformylation reaction is desirably carried out at a total pressure (absolute pressure; hydrogen gas partial pressure plus carbon monoxide partial pressure) of 5 to 300 atmospheres and at a temperature of 80° to 150° C. The hydrogen gas/carbon monoxide gas mole ratio in the charge gas before entering the reactor should desirably be within the range of about 3/1 to about ⅓. The presence in the reaction system of a small amount of a gas inert to the hydroformylation reaction, such as methane, ethane, propane, nitrogen, helium, argon, carbon dioxide and dimethyl ether, will not cause any troubles. While the hydroformylation reaction is desirably carried out in the absence of any solvent, the reaction may also be conducted in the presence of an inert solvent in the hydroformylation reaction. As such solvent, there may be mentioned, among others, alcohols, such as ethanol, butanol, 3-methylbutanol and 3-methylpentane-1,5-diol, saturated aliphatic hydrocarbons, such as pentane, hexane, heptane, octane, nonane and decane, aromatic hydrocarbons, such as benzene, toluene and xylene, esters, such as dioctyl phthalate, and ethers, such as tetrahydrofuran. The presumable precursor of 1,1,7-trimethylolheptane given by the hydroformylation is 2-hydroxymethyl-1,9-nonanedial, which is formed presumably via 9-hydroxy-7-nonenal.

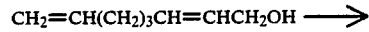

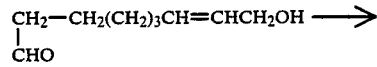

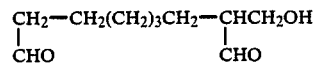

For increasing the yield of such precursor of 1,1,7-trimethylolheptane, it is therefore desirable to conduct the hydroformylation reaction for a sufficiently long time.

The product separation from the thus-obtained hydroformylation reaction mixture is carried out, for example, by removing the hydroformylation catalyst and the solvent (if used) from said reaction mixture by filtration, distillation or some other suitable means. The thus-obtained product is submitted to the next hydrogenation step, generally without isolation of the respective product components.

The hydrogenation of the hydroformylation product is generally carried out in the presence of a hydrogenation catalyst. Any of the hydrogenation catalysts generally used for converting aldehydes to alcohols by hydrogenation may be used as said hydrogenation catalyst. Generally, the use of ruthenium catalysts, such as ruthenium-on-carbon, and nickel catalysts, such as Raney nickel and nickel-on-diatomaceous earth, is advantageous from the industrial viewpoint. The hydrogenation reaction is carried out generally at a hydrogen gas partial pressure of 1 to 200 atmospheres (absolute pressure) and at a temperature of 20° to 200° C. The hydrogenation reaction may be carried out either in the absence of any solvent or in the presence of an inert solvent in the hydrogenation reaction. As such solvent, alcohols, such as ethanol, butanol, 3-methylbutanol and 3-methyl-pentane-1,5-diol, saturated aliphatic hydrocarbons, such as pentane, hexane, heptane, octane, nonane and decane, aromatic hydrocarbons, such as benzene, toluene and xylene, ethers, such as tetrahydrofuran, other organic solvents and water are used either singly or in the form of a mixture of two or more of these.

The product 1,1,7-trimethylolheptane can be isolated by subjecting the hydrogenation reaction mixture to a separation/purification procedure, such as distillation and/or crystallization, following removal of the hydrogenation catalyst and solvent as necessary.

The starting material octa-2,7-dien-1-ol can be readily prepared by dimerization-hydration of butadiene by the method disclosed, for example, in Japanese Laid-open Patent Application Kokai No. 138129/1981.

Process B

The base to be present in the system for the reaction of 1,9-nonanedial with formaldehyde may be any of those bases generally used in reacting aldehydes with formaldehyde to give the corresponding methylol derivatives. Typical examples are hydroxides or carbonates of alkali metal or alkaline earth metal, such as lithium hydroxide, sodium hydroxide, potassium hydroxide, barium hydroxide, calcium hydroxide, lithium carbonate, sodium carbonate and potassium carbonate, heterocyclic, aliphatic or alicyclic tertiary amines or quaternary ammonium salts, such as trimethylamine, triethylamine, tri-n-propylamine, tri-n-butylamine, N-methylpyrrolidine, N-methylpiperidine, N-methylmorpholine, N,N-dimethylcyclohexylamine and tetraethylammonium hydroxide, and anion exchangers, such as Amberlyst A-27 ® (Rohm and Haas). Formaldehyde is generally used in the form of an aqueous solution. As said aqueous solution of formaldehyde, commercially available aqueous solution of formaldehyde having a concentration of 5 to 50 percent by weight can be used as such. For increasing the yield of the 1,1,7-trimethylolheptane precursor, it is preferable to use formaldehyde in an amount of 0.05 to 4 moles per mole of 1,9-nonanedial. The hydroxymethylation reaction can be carried out in the absence of any organic solvent or in the presence of an inert organic solvent in the hydroxymethylation reaction, which may be homogeneous or heterogeneous. The use, as the solvent, of an organic solvent at least partly soluble in water is preferred. As typical examples of such solvent, there may be mentioned lower aliphatic alcohols, such as methanol, ethanol, propanol and butanol, and aliphatic or alicyclic ethers, such as diethyl ether, tetrahydrofuran and dioxane. When the reaction is carried out in an aqueous medium containing a base dissolved therein, for example a hydroxide or carbonate of an alkali metal or alkaline earth metal, a tertiary amine or a quaternary ammonium salt, it is desirable that said base be used in an amount such that the pH of said aqueous medium is within the range of 8 to 13. The reaction temperature should preferably be the range of 5° to 70° C. The 1,1,7-trimethylolheptane precursor can be obtained in high yields within this temperature range.

The product separation from the thus-obtained hydroxymethylation reaction mixture is carried out, for example, by extracting said reaction mixture with an organic solvent, such as diethyl ether. While the 1,1,7-trimethylolheptane precursor contained in the hydroxymethylation reaction product is supposed to be hydroxymethyl-1,9-nonanedial, said product as such is submitted to the next hydrogenation step, generally without isolation of the respective product components.

The hydrogenation of the hydroxymethylation reaction product and the separation and purification of 1,1,7-trimethylolheptane are carried out in the same manner as in the 1,1,7-trimethylolheptane production from the hydroformylation product in the above-mentioned process A.

The starting material 1,9-nonanedial can be readily produced by hydroformylating 7-octenal by the method disclosed, for example, in Japanese Laid-open Patent Application Kokai No. 157739/1983.

1,1,6-Trimethylolheptane and 1,6,6-trimethylolheptane, which are provided by the invention, can be produced, for example, by reacting 2-methyl-1,8-octanedial with formaldehyde in the presence of a base and hydrogenating the reaction product.

The reaction of 2-methyl-1,8-octanedial with formaldehyde is carried out under substantially the same conditions as used for the reaction of 1,9-nonanedial with formaldehyde in the above-mentioned process B. The product separation from the thus-obtained hydroxymethylation reaction mixture is effected, for example, by extracting said reaction mixture with an organic solvent, such as diethyl ether. While the precursor of 1,1,6-trimethylolheptane and 1,6,6-trimethylolheptane as contained in the hydroxymethylation reaction product is supposed to be 2-(hydroxymethyl)-7-methyl-1,8-octanedial or 2-(hydroxymethyl)-2-methyl-1,8-octanedial, the product obtained by said hydroxymethylation reaction is submitted, generally as such, to the next hydrogenation step, without isolation of the respective product components.

The hydrogenation of the hydroxymethylation reaction products and the separation and purification of 1,1,6-trimethylolheptane and 1,6,6-trimethylolheptane from the hydrogenation reaction mixture are carried out in the same manner as in the production of 1,1,7-trimethylolheptane from the corresponding hydroformylation product in the above-mentioned process A.

The starting material 2-methyl-1,8-octanedial can be prepared with ease by hydroformylating 7-octenal by the method disclosed, for example, in Japanese Laid-open Patent Application Kokai No. 157739/1983.

Trimethylolheptanes which have three terminal primary alcohol (hydroxyl)groups and have a structure such that one hydroxyl group is separated from at least one other hydroxyl group by a long carbon chain containing at least 8 carbon atoms [hereinafter each referred to as trimethylolheptane (A)], such as the above-mentioned 1,1,7-trimethylolheptane, 1,1,6-trimethylolheptane and 1,6,6-trimethylolheptane, are useful each as a polyhydric alcohol component for the production of the polyester provided by the invention for achieving some of the above-mentioned objects of the present invention.

The polyester according to the invention is a polyester consisting of a polybasic acid component and a polyhydric alcohol component and is characterized in that said polyhydric alcohol component is composed of 0.5 to 100 mole % of trimethylolheptane (A) or an ester-forming derivative thereof and 99.5 to 0 mole % of at least one other polyhydric alcohol or an ester-forming derivative thereof and in that at least 50% of the terminal functional groups of said polyester are hydroxyl groups.

As examples of trimethylolheptane (A), there may be mentioned not only 1,1,7-trimethylolheptane, 1,1,6trimethylolheptane and 1,6,6-trimethylolheptane but also 1,2,6-trimethylolheptane and 1,2,7-trimethylolheptane. The most preferred one is 1,1,7-trimethylolheptane. Trimethylolheptane (A) may be a mixture of two or more species. 1,1,1-Trimethylolheptane is known in the art as a triol isomeric to trimethylolheptane (A). With said 1,1,1-trimethylolheptane, however, the curing reaction fails to proceed to a satisfactory extent, as will be explained later herein with respect to 1,1,1-trimethylolpropane.

The polyester according to the invention is composed of a polyhydric alcohol component containing trimethylolheptane (A) and a polybasic acid component. Thus, said polyester is obtained by polymerizing, by esterification, such a polyhydric alcohol or an ester-forming derivative thereof and a polybasic acid or an ester-forming derivative thereof. The polyester resin according to the invention includes alkyd resins, oil-free alkyd resins and thermosetting linear polyester resins.

It is important to the polyester according to the invention that at least 50 percent of the polyester terminal functional groups are hydroxyl groups. If the number of such terminal functional groups is insufficient, a sufficient degree of curing cannot be achieved.

As polyhydric alcohols usable in combination with trimethylolheptane (A), there may be mentioned, among others, aliphatic, aromatic or alicyclic dihydric, trihydric and tetrahydric alcohols as well as polyhydric alcohols containing five or more hydroxyl groups.

Examples of the dihydric alcohol are aliphatic diols containing 2 to 12 carbon atoms, such as ethylene glycol, propylene glycol, 1,3-butylene glycol, 1,6-hexanediol, neopentyl glycol, 1,9-nonanediol, 2-methyl-1,8-octanediol and 1,10-decanediol, polyalkylene glycols, such as diethylene glycol, triethylene glycol, polyethylene glycol and dipropylene glycol, long-chain ester diols, such as 2,2-dimethyl-3-hydroxypropyl 2,2-dimethyl-3-hydroxypropionate and 2,3-epoxypropanoyl esters of α-alkyl-$C_{9-11}$ monocarboxylic acids, and aliphatic or aromatic ring-containing diols containing 8 to 40 carbon atoms, such as hydrogenated bisphenol A and bisphenol A dihydroxypropyl ether.

As the trihydric, tetrahydric and other polyhydric alcohols, there may be mentioned, for example, triols, such as glycerin, trimethylolpropane and trimethylolethane, and tetrahydric and further polyhydric alcohols, such as pentaerythritol and dipentaerythritol. Said alcohols may have another substituent, for example an amino group, as in the case of tris(hydroxymethyl)aminomethane.

As preferred examples of the polybasic acid, there may be mentioned aromatic dicarboxylic acids containing 8 to 20 carbon atoms, such as phthalic anhydride, isophthalic acid and terephthalic acid, as well as aliphatic dicarboxylic acids containing 4 to 40 carbon atoms, such as adipic acid, azelaic acid, sebacic acid, succinic acid, suberic acid and decanedicarboxylic acid. The aliphatic dicarboxylic acids may be in the form of a dimer, for example in the case of dioleic acid, dilinolenic acid or a mixture of these, or may be branched. Dimer acids are also included accordingly. Furthermore, as in the case of tetrabromophthalic anhydride or tetrachlorophthalic anhydride, for instance, the aromatic ring or rings may optionally have one or more substituents, such as halogen atoms. Also usable are tetrahydrophthalic anhydride, hexahydrophthalic anhydride, chlorendic anhydride, endic anhydride, maleic anhydride, fumaric acid, itaconic acid, succinic anhydride and the like saturated or unsaturated dicarboxylic acids. Tribasic, tetrabasic and further polybasic acids, such as trimellitic anhydride, methylcyclohexanetricarboxylic anhydride and pyromellitic anhydride.

The term "alkyd resin" as used herein means a resin composed of the main chain of a polyester synthesized from the above-mentioned components and fatty acid side chain bound to said main chain by ester bonding. Generally it is also called "oil-modified polyester resin". The fatty acid side chain source for use in the practice of the invention may be any of those fatty acids or oils generally used for modifying alkyd resins. As such fatty acids, there may be mentioned, for example, aliphatic monocarboxylic acids containing 8 to 20 carbon atoms, such as caprylic acid, capric acid, lauric acid, myristic acid, palmitic acid, stearic acid, oleic acid, ricinolic acid, linolic acid, linolenic acid and eleostearic acid. As the modifying oils, there may be mentioned, among others, castor oil, coconut oil, linseed oil, palm oil, safflower oil, soybean oil, tung oil, dehydrated castor oil and tall oil fatty acids. Any ordinary method of modification which is commonly known to those skilled in the art may be employed as such. Thus, for example, the polyester containing trimethylolheptane (A) may be subjected to said modification or the polyester modified beforehand may be reacted with trimethylolheptane (A).

The polyester according to the invention may also be used as an oil-free alkyd if a long-chain diol is used therein as a component thereof.

The quantity ratio between the polyhydric alcohol and polybasic acid to be used in the production of the polyester according to the invention may be varied as desired depending on the intended use of said polyester and on other factors.

Long-chain aliphatic diols and aliphatic dicarboxylic acids containing 5 or more carbon atoms in their straight chain give flexibility and low-temperature resistance to coat films, while aromatic or cyclohexane ring-containing compounds, such as terephthalic acid, hexanedimethanol, give hardness to coat films. Therefore, for balanced characteristics, it is preferable that the aromatic ring and/or cyclohexane ring concentration in the polyester be within the range of 1.7 to 3.2 moles per kilogram.

The polyester according to the invention is characterized in that said trimethylolheptane (A) is used therein as a branching agent. Therefore, any other branching agent than said trimethylolheptane (A) is essentially unnecessary. However, the use of other branching agents is not prohibited if they are used in amounts in which they will not impair the paint characteristics. Generally, they should be used in amounts not exceeding 50 percent by weight of trimethylolheptane (A).

When the conventional branching agents, such as trimethylolpropane and pentaerythritol, are used, the reactivity of the third hydroxyl group remaining after the adjacent two hydroxyl groups have reacted is very much restricted by steric hindrance. Therefore, polyesters synthesized from these polyhydric alcohols have hydroxyl groups reacting more slowly in curing as compared with other terminal hydroxyl groups and, moreover, said polyhydric alcohols cannot work effectively as a branching agent. On the contrary, trimethylolheptane (A) is used as a branching agent in the polyester according to the invention. Said trimethylolheptane (A) is characterized in that all the terminal hydroxyl groups are primary alcohol groups and in that one of the hydroxyl groups is separated from other two hydroxyl groups by a long methylene chain (inclusive of a methine chain). Therefore, the three hydroxyl groups are very close in reactivity to one another. Trimethylolheptane (A), which is to be used in the polyester according to the invention, has a long methylene chain (inclusive of a methine chain) and therefore can lower the glass transition temperature of the polyester and give coat films having flexibility and low-temperature resistance without decreasing the hardness of the coat films.

The method of producing the polyester according to the invention is not critical. Thus, for example, said polyester can be synthesized by the methods described in the monograph "Toryoyo Gosei Jushi Nyumon (Introduction to Synthetic Resins for Paints)", pages 123–127, published by Kobunshi Kanko Kai, 1974. In carrying out the polymerization or transesterification reaction, various catalysts, stabilizers, modifiers, additives and other auxiliaries may be used.

The polyester according to the invention can have, as desired, a molecular weight ordinary in paint resins in general. A preferred molecular weight is within the range of 500 to 30,000 as expressed in terms of number average molecular weight. Generally, alkyd resins have a molecular weight of 500 to 3,000. Oil-free alkyds have a number average molecular weight of 500 to 30,000. Therefore, such ranges are preferred also in the practice of the invention. An excessively high molecular weight will result in an increased solution viscosity and may render the paint preparation and application difficult.

Generally, the terminal reactive groups of polyester are for the most part hydroxyl groups or carboxyl groups remaining unreacted in esterification. If the number of such hydroxyl groups is excessively small, the curing reaction will not proceed to a satisfactory extent. On the contrary, if the number of carboxyl groups is excessively great, foaming may occur in the step of curing and this makes the polyester unsuited for use in paints. Therefore, at least 50 percent, preferably 90 percent or more, of the terminal functional groups in the polyester must be hydroxyl groups. When the absolute number of hydroxyl groups is small, the same drawbacks as mentioned above are encountered. Therefore, the hydroxyl value of the polyester should preferably be not less than 5 mg KOH per gram of polymer. The upper limit of the hydroxyl value is dependent on the molecular weight, branching agent concentration and acid value and should preferably be not more than 350 mg KOH per gram. The acid value of these polyesters is not higher than the hydroxyl value and should preferably be not more than 20 mg KOH per gram in the case of alkyds and not more than 10 mg KOH per gram in the case of oil-free alkyds.

Various solvents can be used for dissolving the polyester according to the invention and, as examples, there may be mentioned those solvents generally usable as paint solvents. Typical examples are hydrocarbons, such as toluene, xylene, solvent naphtha, cyclohexane and decalin, halogenated hydrocarbons, such as trichloroethylene and trichloroethane, alcohols, such as butanol, isopropanol, diethylene glycol and hexanol, esters, such as ethyl acetate, amyl acetate and butyl acetate, ketones, such as acetone and methyl ethyl ketone, and ethers, such as dioxane and ethylene glycol monobutyl ether.

The polyester according to the invention can be used in various fields of application according to the same formulation ideas and techniques as for general alkyd resins, oil-free alkyd resins and linear polyester resins. Thus, for example, said polyester may be used efficiently in preparing paints for railroads, automobiles, electric appliances, machines, metal goods and so forth when it is a short oil alkyd, in preparing paints for buildings, ships, vehicles, machines and so forth when it is a medium oil alkyd, in preparing paints for buildings, ships, metal goods and so forth when it is a long oil alkyd, and in preparing paints for vehicles, electric appliances, metal goods and so forth when it is an oil-free alkyd or high-molecular-weight oil-free alkyd. When said polyester is an oil-free alkyd or high-molecular-weight oil-free alkyd, it has good processability and is therefore used in the form of paints for metal coating, in particular for producing the so-called precoated metal sheets.

Thus, the polyester according to the invention can be made up into paints by admixing with a color pigment, dye, curing agent, catalyst, dispersant and so on, followed by agitation for dispersion. In said paints, the above-mentioned polyester generally accounts for 60 to 95 percent by weight of the vehicle fraction and the curing agent for 5 to 40 percent by weight.

The thus-obtained paints are applied to various materials in the conventional manner, for example by brush coating, roller coating or spray coating, to give coat films.

The curing agent may be any of the curing agents usable in polyester resins in general. Among others, amino resins (aminoplasts), such as methyl-etherified methylolmelamine, butyl-etherified methylolmelamine and butylated benzoguanamine resin, give paints capable of forming coat films having good transparency, luster, hardness, wear resistance, weather resistance and chemical resistance. Therefore, such paints are used mainly for coating automobiles, electric appliances, railroads, vehicles and other metal products. On the other hand, paints in which a polyisocyanate, such as trimethylolpropane-hexamethylene diisocyanate adduct, water-hexamethylene diisocyanate adduct condensate, hexamethylene diisocyanate trimer and trimethylolpropane-tolylene diisocyanate adduct, is used are superior in coat film flexibility. Said paints can be used for coating various metal, plastic, wood and other materials.

The polyester according to the invention is used, for example, in the form of (1) nonsolvent paints without using any solvent, (2) solution paints after dilution with a solvent, (3) baking paints by blending with an amino resin and (4) two-component system paints with a polyisocyanate as the curing agent.

Trimethylolheptanes represented by the 1,1,7-trimethylolheptane, 1,1,6-trimethylolheptane and 1,1,6-trimethylolheptane according to the invention [hereinafter collectively referred to as trimethylolheptane (B)] are useful as alcohol components for the production of trimethylol heptane tri(meth)acrylates to be provided for achieving some of the afore-mentioned objects of the present invention.

Trimethylolheptane tri(meth)acrylates according to the invention are novel compounds. Said novel compounds include various isomers. They are, for instance, 1,1,7-trimethylolheptane tri(meth)acrylate, 1,1,1-trimethylolheptane tri(meth)acrylate, 1,1,6-trimethylolheptane tri(meth)acrylate, 1,2,7-trimethylolheptane tri(meth)acrylate, 1,6,6-trimethylolheptane tri(meth)acrylate and 1,2,6-trimethylolheptane tri(meth)acrylate. 1,1,7-Trimethylolheptane tri(meth)acrylate has the following general formula:

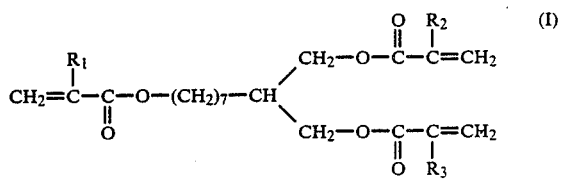

wherein $R_1$, $R_2$ and $R_3$ are the same or different and each is a hydrogen atom or a methyl group.

Said novel compounds can be obtained by reacting the corresponding trimethylolheptane (B) with acrylic or methacrylic acid or an ester-forming derivative thereof.

Other examples of trimethylolheptane (B) than 1,1,7-trimethylolheptane, 1,1,6-trimethylolheptane and 1,6,6-trimethylolheptane are 1,1,1-trimethylolheptane, 1,2,6-trimethylolheptane and 1,2,7-trimethylolheptane. 1,1,1-Trimethylolheptane is a known compound and can be readily produced by, for example, hydroxymethylation of octylaldehyde.

The trimethylolheptane triacrylates according to the invention have very low skin irritating activity as compared with trimethylolpropane triacrylate. Thus, for example, trimethylolpropane triacrylate has a P.I.I. of 4.8, while 1,1,7-trimethylolheptane triacrylate, one of the compounds according to the invention, has a P.I.I. of 2.7. The P.I.I. value of 1,1,1-trimethylolheptane triacrylate is as low as 2.3 and this is of great importance.

Furthermore, the tri(meth)acrylates according to the invention have very good reactivity (rate of curing and ultimate conversion) as compared with trimethylolpropane tri(meth)acrylate. In particular, it is surprising that 1,1,1-trimethylolheptane tri(meth)acrylate, which is structurally close to trimethylolpropane tri(meth)acrylate, has good reactivity.

Furthermore, 1,1,7-trimethylolheptane triacrylate has a viscosity as low as 33 centipoises (25° C.), which is very low as compared with the viscosity [125 centipoises (25° C.)] of trimethylolpropane triacrylate. The viscosity of 1,1,1-trimethylolheptane triacrylate is low, namely 172 centipoises (25° C.), and this triacrylate is useful as a diluent for high-viscosity prepolymers, such as polyurethane acrylates, epoxy acrylates and polyester acrylates.

As far as the conventional polyfunctional monomer trimethylolpropane tri(meth)acrylate is concerned, the reactivity of the third (meth)acryloyl group remaining after the adjacent two other (meth)acryloyl groups have reacted is suppressed to a great extent due to the resulting steric hindrance. Therefore, in the conventional tri(meth)acrylate, two(meth)acryloyl groups alone can react readily, while the remaining one (meth)acryloyl group tends to remain unreacted. As a result, such tri(meth)acrylate not only has a (meth)acryloyl group reacting slowly in curing as compared with other terminal (meth)acryloyl groups but also cannot serve efficiently as a curing agent. On the contrary, the trimethylolheptane tri(meth)acrylates according to the invention which have (meth)acryloyloxy groups separated by a long carbon chain are effective as curing agents. Thus, said trimethylolheptane tri(meth)acrylates are characterized in that one terminal (meth)acryloyloxy group is separated from the other two (meth)acryloyloxy groups by a long methylene chain (inclusive of a methine chain). Therefore, the three (meth)acryloyl groups are very close in reactivity to one another. Furthermore, 1,1,1-trimethylolheptane tri(meth)acrylate provided by the present invention is faster in rate of curing and higher in ultimate attainable conversion as well than trimethylolpropane tri(meth)acrylate although it is structurally close to trimethylolpropane tri(meth)acrylate. Therefore, it is effective as a reactive diluent like those tri(meth)acrylates which have (meth)acryloyloxy groups separated by a long carbon chain.

The long carbon chain-containing trimethylolheptane tri(meth)acrylates to be used in accordance with the invention, because of their having said long methylene chain (inclusive of a methine chain), give resins having a low glass transition temperature and capable of giving flexible and low-temperature-resistant moldings or coat films. The surface hardness of the moldings obtained shows no decrease since the curing reaction can proceed smoothly.

The trimethylolheptane tri(meth)acrylates according to the invention can be produced, for example, by reacting a corresponding trimethylolheptane with acrylic or methacrylic acid or an ester-forming derivative thereof, if necessary in the presence of a catalyst and/or a solvent. As the ester-forming derivative, there may be mentioned known (meth)acrylate esters, such as methyl, ethyl, n-propyl and isopropyl esters, and (meth)acrylic acid halides, among others.

Said reaction may include the following modes:
(1) Condensation under dehydration of acrylic or methacrylic acid and trimethylolheptane (B);
(2) Transesterification, or ester exchange, between a lower alkyl acrylate or methacrylate and trimethylolheptane (B); and
(3) Condensation under elimination of hydrogen chloride of acryloyl or methacryloyl chloride and trimethylolheptane (B).

Trimethylolheptane (B) is characterized in that all the three hydroxyl groups thereof are primary and have very good reactivity. Therefore, the rate of the esterification reaction with acrylic or methacrylic acid or the like is fast and the corresponding tri(meth)acrylate can be synthesized with ease in the above modes of reaction. In particular, when at least one pair of hydroxyl groups out of the three methylol groups are separated from each other by a long carbon chain, as in the case of 1,1,7-trimethylolheptane, 1,1,6-trimethylolheptane, 1,2,7-trimethylolheptane, 1,2,6-trimethylolheptane and 1,6,6-trimethylolheptane, the rate of esterification reaction becomes very fast.

The above mode (1) is described in more detail in the following.

A trimethylolheptane having the desired structural formula and acrylic acid (and/or methacrylic acid) are charged into an inert solvent, such as benzene, toluene, xylene, n-hexane, methyl isobutyl ketone or cyclohexanone, and the esterification is carried out under reflux in the manner of dehydration condensation. p-Toluenesulfonic acid, sulfuric acid or the like may be used as a catalyst. For eliminating the water resulting from esterification out of the system, it is recommendable to use an organic solvent capable of forming an azeotrope with water. After the reaction, the desired trimethylolheptane tri(meth)acrylate can be separated and purified in the conventional manner, for example by washing with an aqueous alkali solution, washing with water, drying, solvent removal and so forth. Distillation may be employed as an alternative method of purification.

The reaction is recommendably carried out in the presence of a polymerization inhibitor. The polymerization inhibitor is not limited to any particular species but should preferably be removable in the step of washing with an aqueous alkali solution. Hydroquinone, p-methoxyphenol and cuprous chloride are thus preferred examples. While the above-mentioned examples of the solvent are all inert solvents, methyl (meth)acrylate itself may be used also as a solvent.

The transesterification [mode (2)] mentioned above is now described in further detail.

A (meth)acrylate ester, such as methyl acrylate, methyl methacrylate, ethyl acrylate, ethyl methacrylate, propyl acrylate or propyl methacrylate, and trimethylolheptane (B) are heated in the presence of a catalyst while the byproduct lower alcohol is removed from the reaction system for promoting the transesterification reaction. Usable as the catalyst are, for example, sulfuric acid, p-toluenesulfonic acid, metallic sodium, sodium alcoholate, tetraalkoxytitanium, aluminum alcoholate and magnesium alcoholate. Also usable are metal acetylacetonates, tin carboxylates and the like. A polymerization inhibitor is generally added to the reaction system. As said polymerization inhibitor, there may be mentioned, for example, hydroquinone, p-methoxyphenol, tert-butylcatechol, p-phenylenediamine and phenyl-$\beta$-naphthylamine.

The trimethylolheptane tri(meth)acrylates according to the invention can be used, for example, as raw materials or modifiers for use in inks, adhesives, coating compositions, printing materials, electronics-related materials, paints, molding resins and so forth in the same manner as the ordinary tri(meth)acrylate monomers. Compositions containing any of said tri(meth)acrylates according to the invention as an essential component are particularly useful as resin compositions curable upon exposure to heat or radiations, such as ultraviolet rays or electron beams. In particular, compositions derived therefrom by adding a radiation-curable prepolymer and/or some other polymerizable monomer together with one or more compounds selected from among photoinitiators, photosensitizers, colorants, other resins inert to radiations, fillers and so forth show radiation curability. The content of the tri(meth)acrylate according to the invention is within the range of 5 to 99.9 percent by weight on the resin composition. Since the trimethylolheptane tri(meth)acrylates according to the invention have a low viscosity and low skin irritating activity, said compositions have good workability and can be handled with ease. Said tri(meth)acrylates can be cured at a high rate, and coat films obtained after curing of said compositions are characterized by excellent hardness, toughness, pliability and durability.

The tri(meth)acrylates according to the invention may be used in the form of a mixture of isomers. In particular, long carbon chain-containing trimethylolheptanes are obtained in certain instances in the form of a mixture for reactivity reasons. Such mixture as such may be subjected to (meth)acryloyl group introduction and the resulting (meth)acrylate mixture can be used as a raw material or reactive diluent in preparing the resin compositions mentioned above.

The prepolymer mentioned above includes polymers having a plurality of polymerizable, ethylenically unsaturated groups. Typical examples are (1) polyester compounds having a plurality of vinyl groups as obtained by condensation oligomerization of a polyhydric alcohol with a polybasic acid and an ethylenically unsaturated monocarboxylic acid, (2) epoxy compounds having a plurality of vinyl groups as obtained by addition of an ethylenically unsaturated carboxylic acid to a polyfunctional epoxy compound and (3) polyurethane compounds having a plurality of vinyl groups as obtained by addition reaction between a polyfunctional isocyanate and an active hydrogen-containing, ethylencially unsaturated monomer.

Representative of these prepolymers are the so-called acrylic oligomers. According to the structure of the backbone-forming molecule, said acrylic oligomers may be classified into polyester (meth)acrylates, polyurethane (meth)acrylates, epoxy (meth)acrylates, alkyd (meth)acrylates, polyether (meth)acrylates, polyol (meth)acrylates, etc. Particularly preferred among these are polyester (meth)acrylates, polyurethane (meth)acrylates and epoxy (meth)acrylates. These prepolymers are satisfactorily compatible with the trimethylolheptane tri(meth)acrylates according to the invention and have a good viscosity-reducing effect. Therefore, particularly good workability can be attained with them. Radiation-curable resin compositions containing said essential components can give coat films having an appropriate hardness and excellent toughness, pliability, adhesion and durability.

The polyester (meth)acrylates can be obtained from a polyhydric alcohol, a polybasic acid (or the anhydride thereof) and (meth)acrylic acid. The epoxy (meth)acrylates can be produced by the addition reaction of the epoxy groups of an epoxy resin with (meth)acrylic acid or a (meth)acrylate having a terminal carboxyl group. The polyurethane (meth)acrylates can be prepared by reacting a hydroxyl group-containing (meth)acrylate with an isocyanate compound. These are generally called prepolymers because their molecular weight is not sufficiently high. Sometimes they are also called base resins. These prepolymers generally have a molecular weight within the range of 500 to 20,000.

The above-mentioned polymerizable monomer to be used in the practice of the invention is capable of serving as a diluent for such prepolymers and itself is capable of polymerizing upon exposure to radiations. Therefore, said monomer is sometimes called "reactive diluent". The polymerizable monomer may be used for the purpose of promoting the polymerization reaction. The trimethylolheptane tri(meth)acrylates according to the invention, when incorporated as such polymerizable monomers in appropriate resin compositions, can work effectively. In the practice of the invention, other polymerizable monomers than the above-mentioned tri(meth)acrylates may be used in combination with the latter. Low-viscosity polymerizable monomers generally available in the market as such can be used as said other polymerizable monomers. Representative of said other polymerizable monomers are (meth)acryloyl group-containing compounds, which include all commercially available (meth)acrylic monomers, inclusive of monofunctional monomers having one (meth)acryloyl group and polyfunctional monomers having two or more acryloyl groups. Typical examples are trimethylolpropane tri(meth)acrylate, pentaerythritol tri(meth)acrylate, diethylene glycol di(meth)acrylate, triethylene glycol di(meth)acrylate, polyethylene glycol di(meth)acrylate, ethyl carbitol (meth)acrylate, neopentyl glycol di(meth)acrylate and 1,6-hexanediol di(meth)acrylate. (Meth)acrylic amides, such as (meth)acrylamide and N-methyl(meth)acrylamide, and non-(meth)acrylic polymerizable monomers, such as styrene, acrylonitrile and N-vinylpyrrolidone, may also be used additionally. These other polymerizable monomers are used in an appropriate amount which should be determined depending on the purpose for which they are used.

The photoinitiator is used for absorbing ultraviolet rays and the like radiations and thereby initiating the polymerization reaction. It is used in the case of ultraviolet curing. The technology of ultraviolet curing is well known in the art and the tri(meth)acrylates according to the invention can be cured by known ultraviolet curing techniques. The photoinitiator to be used in ultraviolet-curable resin compositions is not limited to any particular species but is generally required to show good storage stability after incorporation into the compositions. As such photoinitiator, there may be mentioned, among others, benzoin alkyl ethers, such as benzoin ethyl ether, benzoin butyl ether and benzoin isopropyl ether, propiophenones, such as 2-hydroxy-2-methylpropiophenone, 4'-isopropyl-2-hydroxy-2-methylpropiophenone and 4'-dodecyl-2-hydroxy-2-methylpropiophenone, benzyl dimethyl ketal, 1-hydroxycyclohexyl phenyl ketone, anthraquinones, such as 2-ethylanthraquinone and 2-chloroanthraquinone, and (thio)xanthones, such as xanthone, thioxanthone, 2-chlorothioxanthone and 2-isopropylthioxanthone. Furthermore, ordinary photoinitiators, for example benzophenones, such as benzophenone, Michler's ketone and methyl o-benzoylbenzoate, acetophenones, such as 2,2-diethoxyacetophenone, 4'-phenoxy-2,2-dichloroacetophenone, trichloroacetophenone, p-t-butyltrichloroacetophenone and 2,2-dimethoxy-2-phenylacetophenone, and benzil, may also be used. As particularly preferred initiators among these, there may be mentioned benzyl dimethyl ketal, 1-hydroxycyclohexyl phenyl ketone and the like.

These photoinitiators may be used in the conventional manner either singly or in the form of a mixture of two or more in any desired mixing ratio. They are used in an amount within the range of 0.1 to 10 percent by weight on the resin composition basis. Preferably, they are used in an amount of 0.1 to 10 percent by weight, more preferably 1 to 5 percent by weight, on the coating composition basis.

The photoinitiator mentioned above may include a photosensitizer, as the case may be. The photosensitizer itself cannot be activated by ultraviolet rays but, when used in combination with a photoinitiator, can promote the initiation of photopolymerization more than when the photoinitiator alone is used. Amine compounds, sulfur compounds and phosphorus compounds, for instance, can produce such an effect. More specifically, there may be mentioned triethylamine, alkylmorpholine, triethylenetetramine, diethylaminoethyl methacrylate, organic colorants, perylene, anthracene and thioxanthone derivatives. These may be used either singly or in admixture. Radiation-curable resin compositions are preferably composed of 5 to 99.9 percent by weight of trimethylolheptane tri(meth)acrylate, 0.1 to 10 percent by weight of photoinitiator and 0 to 95 percent by weight of radiation-curable prepolymer and/or polymerizable monomer other than said tri(meth)acrylate.

When the tri(meth)acrylates according to the invention are used as heat-curable resin compositions, ordinary radical initiators are used and, if necessary, radical polymerization promoters may recommendably be used additionally. As said radical initiators, there may be mentioned benzoyl peroxide, methyl ethyl ketone peroxide, lauroyl peroxide, cyclohexanone peroxide, di-t-butyl peroxide, di-t-amyl peroxide, dicumyl peroxide, t-butyl perbenzoate, cumene hydroperoxide and azobisisobutyronitrile, among others. They are used in an amount within the range of 0.01 to 1 percent by weight on the resin composition basis. As said radical polymerization promoters, there may be mentioned organic metal salts, such as cobalt octoate, iron octoate, manganese octoate, vanadium octoate and cobalt naphthenate, and organic amines, such as N,N-dimethylaniline.

The resin compositions may contain other resins, for example epoxy resins, urethane resins, polyester resins and waxes, as desired depending on the purpose for which said compositions are used. The above resin compositions may further contain colorants, solvents, plasticizers, leveling agents, thixotropic agents, anticissing agents, anti-blocking agents, silane coupling agents, polymerization inhibitors, anti-oxidants, talc, mica, calcium carbonate, alumina, glass powder, titanium oxide, zinc white, other pigments or fillers, reinforcing materials, and dyes.

The thus-obtained resin compositions can be used in the fields of paints, coatings, inks, printing materials, adhesives and coating for various electronics-related materials or optical fibers, for instance, giving high-performance coat films having many characteristic features. Thus they have very great utility.

The following examples will illustrate the invention in further detail. They are, however, by no menas limitative of the scope of the invention. In the example, unless otherwise specified, "part(s)" and "%" are "part(s) by weight" and "% by weight", respectively. Physical characteristics measurements were made by the following methods:

(1) Molecular weight

The hydroxyl value and acid value of the resin were measured and the molecular weight was calculated as follows:

$$M \text{ (molecular weight)} = \frac{56.160 \, (2 + \alpha \, (n + 1))}{OHV + AV}$$

where
OHV: Hydroxyl value (mg KOH/g)
AV : Acid value (mg KOH/g)
α: Mole fraction of trifunctional component as calculated on the basis of number of moles of total glycol
N: Number of repeating units [(acid-glycol) being taken as one unit]

(2) Melt viscosity

The melt viscosity measurement was performed at 70° C. using as E type viscometer (Tokyo Keiki).

(3) Glass transition temperature

A Rigaku model DSC TAS100 differential scanning calorimeter was used. The sample (about 10 mg) was cooled to −90° C. and then the temprature was raised at a rate of 20° C. per minute. The middle point of the transition temperature region recorded was read and reported as the glass transition temperature.

(4) Hardness (pencil hardness)

The paint was applied to a glass sheet and, after drying, the hardness was measured according to JIS K-5400. The hardness of the hardest pencil that failed to give any scratch to the coat film was reported as the pencil hardness.

(5) Rate of curing reaction

The infrared absorption spectrum of the paint applied to a sodium chloride disk was measured before and after curing. The rate of hydroxyl group disappearance was calculated in terms of residual hydroxyl group percentage using the absorbance due to hydroxyl at 3350 cm$^{-1}$, with the absorbance due to carbonyl at 1720 cm$^{-1}$ as a standard, as follows:

Residual percentage (%) =

$$\left(1 - \frac{D_{03350}/D_{01720} - D_{3350}/D_{1720}}{D_{03350}/D_{01720}}\right) \times 100$$

where
$D_{03350}$: Absorbance at 3350 cm$^{-1}$ before curing
$D_{01720}$: Absorbance at 1720 cm$^{-1}$ before curing
$D_{3350}$ : Absorbance at 3350 cm$^{-1}$ after curing
$D_{1720}$ : Absorbance at 1720 cm$^{-1}$ after curing The rate of isocyanato group disappearance was determined in the same manner based on the absorbance due to isocyanato group at 2280 cm$^{-1}$.

(6) Tα

The sample was applied to a tinplate and dried and, then, Tα measurement was performed using Toyo Sokki model Vibron DDV-II direct-reading dynamic viscoelasticity measuring apparatus (110 Hz).

(7) Flexing resistance

Coated steel sheets were bent to an angle of 180° and examined for occurrence or nonoccurrence of cracking at the bent portion. The evaluation result "1T" means that the bent portion did not show any abnormality even when only one 0.3 mm thick sheet was inserted at the time of bending.

(8) Reduced viscosity

The polyester sample (0.1 g) was dissolved in 25 ml of a mixed solvent composed of phenol and tetrachloroethane (6/4 by volume) and the reduced viscosity was measured at 30° C.

EXAMPLE 1

A one-liter autoclave equipped with a stirrer, gas inlet, temperature controller and sampling outlet was charged with 500 g of octa-2,7-dien-1-ol, 3.7 mg of dicarbonylacetylacetonatorhodium, 1.38 g of tris(o-t-butylphenyl) phosphite and 0.17 g of triethanolamine and the internal atmosphere of the autoclave was thoroughly replaced with a hydrogen-carbon monoxide gas (mole ratio 2:1). Then, the internal pressure of the autoclave was maintained at 90 atmospheres (gage pressure) with the same gas, the reaction was conducted with stirring at 100° C. for 10 hours. Using a thin-film evaporator, the resulting hydroformylation reaction mixture was treated at 150° C. under a pressure of 1 mmHg (absolute pressure) to separate the catalyst. The procedure gave 665 g of distillate.

A two-liter autoclave equipped with a stirrer, hydrogen gas inlet, starting material inlet, temperature controller and sampling port was charged with 500 ml of n-butanol, 23 g of nickel-diatomaceus earth and 50 ml of water and the internal atmosphere was thoroughly replaced with hydrogen gas. Then, while the internal pressure of the autoclave was maintained at 9 atmospheres (gage pressure) with hydrogen gas, the reaction system was heated to 160° C. with stirring. Then, the distillate obtained above was fed continuously to the autoclave at a rate of 170 ml/hr. During this addition, the pressure and temperature were kept constant. After completion of the addition, the reaction was further continued for 1 hour. The nickel-diatomaceus earth was filtered off from the resulting hydrogenation reaction mixture and the n-butanol was removed from the filtrate using a rotary evaporator. Analysis of 730 g of the residue by gas chromatography revealed that 1,1,7-trimethylolheptane accounted for 27% of the above residue. This residue was distilled under reduced pressure to recover 380 g of a fraction boiling at 168°-170° C. under the pressure of 1 mm Hg (absolute pressure). When this fraction was allowed to stand at room temperature, crystals separated out gradually. The crystals were collected by filtration and washed with tetrahydrofuran-diethyl ether (50:50, v/v). The above procedure yielded 118 g crystals of 1,1,7-trimethylolheptane having the following physical properties.

Elemental analysis: C 63.5%, H 11.5%, O 25.0%
(Calculated for $C_{10}H_{22}O_3$: C 63.1%, H 11.6%, O 25.2%).
Mass spectrum: FD/MS 191 (M+1).
Hydroxyl value: 878 mg KOH/g.
$^1$H-NMR spectrum (CDCl$_3$/DMF—d$_6$) δ ppm
3.5–3.64 (dd, 2H, >CH C$\underline{H}_2$—OH),
3.52–3.66 (dd, 2H, >CHC$\underline{H}_2$—OH),
3.5 (t, 2H, —CH$_2$—C$\underline{H}_2$—OH), $$1.6 \text{ (m, 1H, } -\overset{|}{\underset{|}{C}}-H),$$

1.47 (m, 2H, —C$\underline{H}_2$CH$_2$—OH),
1.15–1.37 (m, 10$\underline{H}$, —(C$\underline{H}_2$)$_5$—CH<).

EXAMPLE 2

A one-liter three-necked flask fitted with a stirrer, thermometer, reflux condenser and drip funnel was filled with 156 g (1 mole) of 1,9-nonanedial, 86 g of a 35 wt.% aqueous solution of formaldehyde (1 mole as formaldehyde) and 200 ml of diethyl ether. At a constant internal temperature of 30°–35° C., the mixture was stirred vigorously and 100 g of a 10 wt. % aqueous solution of sodium carbonate was added dropwise over a period of 2 hours. After completion of the addition, the mixture was further stirred for 12 hours. The resulting reaction mixture was extracted with 100 ml of diethyl ether 3 times. The extracts were collected and using an evaporator, the diethyl ether was distilled off to recover 181 g of a residue.

A one-liter autoclave equipped with a stirrer, hydrogen gas inlet, starting material inlet, temperature controller and sampling port has charged with 300 ml of n-butanol, 5 g of 5 wt. % ruthenium-on-carbon and 10 ml of water, and the internal atmosphere of the autoclave was thoroughly replaced with hydrogen gas. Then, while the internal pressure of the autoclave was maintained under 9 atmospheres (gage pressure) with hydrogen gas, the temperature was increased to 110° C. under stirring. Then, the residue recovered by the above-mentioned evaporation procedure was continuously fed to the autoclave at a rate of 50 ml/hr. During this addition, the pressure and temperature were kept constant. After completion of the addition, the reaction was further carried out for 1 hour. From the resulting hydroformylation reaction mixture, the ruthenium-on-carbon was filtered off and using a rotary evaporator, the n-butanol was removed from the filtrate. The resulting residue, weighing 195 g, was subjected to vacuum distillation to recover a fraction boiling at 167°–171° C. under the pressure of 1 mmHg (absolute pressure). In this manner, 57 g of 1,1,7-trimethylolheptane having the following physical properties was obtained. As analyzed by gas chromatography, the purity of this 1,1,7-trimethylolheptane was 98%.

Elemental analysis: C 63.3%, H 11.8%, O 24.9%
(Calculated for $C_{10}H_{22}O_3$: C 63.1%, H 11.6%, O 25.2%).
Mass spectrum: FD/MS 191 (M+1)
Hydroxyl value: 880 mg KOH/g.
$^1$H—NMR spectrum (CDCl$_3$/DMF—d$_6$) δ ppm
3.5–3.64 (dd, 2H, >CHC$\underline{H}_2$—OH),
3.52–3.66 (dd, 2H, >CHC$\underline{H}_2$—OH),
3.5 (t, 2H, —CH$_2$CH$_2$—O$\underline{H}$), $$1.6 \text{ (m, 1H, } -\overset{|}{\underset{|}{C}}-H),$$

1.5 (m, 2H, —C$\underline{H}_2$CH$_2$—OH),
1.15–1.37 (m, 10$\underline{H}$, —(C$\underline{H}_2$)$_5$—CH<)

REFERENCE EXAMPLE 1

A 100 ml three-necked flask fitted with a liquid-liquid separator for removal of producing water, cooler-condenser, thermometer and stirrer was filled with 7.06 g (37 mmoles) of 1,1,7-trimethylolheptane, 17.2 g (0.15 mole) of caproic acid and 20 ml of benzene and while this mixture was boiled in a nitrogen atmosphere, 0.41 g of p-toluenesulfonic acid was added. The producing water was removed azeotropically with benzene through the liquid-liquid separator. In the course of esterification reaction under the above conditions, the reaction mixture was monitored by gas chromatography. The percent residue of 1,1,7-trimethylolheptane was not more than 1% after 3 minutes of reaction, indicating that almost all the 1,1,7-trimethylolheptane charge was esterified within 3 minutes. One hour after the start of reaction, the proportion of the 1,1,7-trimethylolheptane monoester was not more than 1% of the 1,1,7-trimethylolheptane charge. Thus, about 99% of the starting material 1,1,7-trimethylolheptane was either diesterified or triesterified within 1 hour. Four hours after commencement of the reaction, the proportion of 1,1,7-trimethylolheptane diester was not more than 1% of the initial charge, with about 99% of the starting material 1,1,7-trimethylolheptane having been triesterified.

REFERENCE EXAMPLE 2

The esterification reaction of Reference Example 1 was repeated except that 5.0 g (37 mmoles) of 1,1,1-trimethylolpropane was used in lieu of 7.06 g (37 mmoles) of 1,1,7-trimethylolheptane. The percent residue of 1,1,1-trimethylolpropane at 6 minutes after initiation of the reaction was not more than 1%, indicating that almost all the starting material had been esterified. At 2 hours after initiation of the reaction, the amount of 1,1,1-trimethylolpropane monoester was not more than 1% 1,1,1-trimethylolpropane charge, indicating that about 99% of the starting material 1,1,1-trimethylolpropane had been converted to diester or triester. At 4 hours after the beginning of the reaction, the amounts of the diester and triester were 11% and 88%, respectively, based on the 1,1,1-trimethylpropane charge. At 8 hours, the amount of 1,1,1-trimethylolpropane diester was not more than 1% of the 1,1,1-trimethylolpropane charge, indicating that about 99% of the charge had been converted to the triester.

EXAMPLE 3

A one-liter three-necked flask fitted with a stirrer, thermometer, reflux condenser and dropping funnel was charged with 156 g (1mole) of 2-methyl-1,8-octanedial, 86 g of a 35% aqueous solution of formaldehyde (1 mole as formaldehyde) and 200 ml of diethyl ether. At a constant internal temperature of 30°–35° C., the mixture was stirred vigorously and 100 g of a 10% aqueous solution of sodium carbonate was added dropwise over 2 hours. After completion of the dropping, the mixture was further stirred for 12 hours. The resulting reaction mixture was extracted with three 100-ml portions of diethyl ether. The extracts were combined and the diethyl ether was distilled off using an evaporator, whereby 175 g of a residue was obtained.

A one-liter autoclave fitted with a stirrer, hydrogen gas inlet, temperature controller and sampling port was charged with 300 ml of n-butanol, 5 g of ruthenium-on-carbon and 10 ml of water and the internal atmosphere of the autoclave was thoroughly replaced with hydrogen gas. Then, while the internal pressure of the autoclave was maintained under 9 atmospheres (gage pressure) with hydrogen gas, the temperature was raised to 110° C. under stirring. Then, the residue obtained in the above-mentioned evaporation procedure was continuously fed to the autoclave at a rate of 50 ml/hr. During this addition, the pressure and temperature were kept constant. After completion of the addition, the reaction was further carried out for 1 hour. The rutheium-on-carbon was filtered off from the resulting hydrogenation reaction mixture, and the n-butanol was distilled off from the filtrate using a rotary evaporator. The thus-obtained residue (190 g) was distilled under reduced pressure to recover 38 g of a mixture of 45% of 1,6,6-trimethylolheptane and 55% of 1,1,6-trimethylolheptane as a fraction boiling at 145°–161° C. under the pressure of 1 mm Hg (absolute pressure).

A small amount of this mixture was subjected to preparative gas chromatography [column packing: Silicone GE SE 33, 5% Chromosorb W(GasChro Kogyo); column length: 2 m; column temperature: raised from 120° C. to 250° C.], and 1,6,6-trimethylolheptane and 1,1,6-trimethylolheptane were respectively isolated. These isolates were analyzed. The results obtained are shown below.

(I) 1,6,6-Trimethylolheptane

Elemental analysis: C 62.5%, H 12.0%, O 24.8% (Calculated for $C_{10}H_{22}O_3$: C 63.1%, H 11.6%, O 25.2%).
Mass spectrum: FD/MS 191 (M+1).
$^1$H-NMR spectrum (CDCl$_3$/DMF—d$_6$): δ ppm
3.5 (t, 2H, —CH$_2$C$\underline{H}_2$OH),

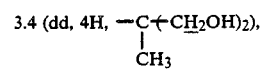
3.4 (dd, 4H, —C(CH$_2$OH)$_2$), CH$_3$ 1.5 (m, 2H, —C$\underline{H}_2$CH$_2$OH),
1.15–1.37 (m, 8, —(CH$_2$)$_4$—),
0.9 (s, 3H, CH$_3$—).

(II) 1,1,6-Trimethylolheptane

Elemental analysis: C 63.0%, H 11.0%, O 25.2% (Calculated for $C_{10}H_{22}O_3$: C 63.1%, H 11.6%, O 25.2%).
Mass spectrum: FD/MS 191 (M+1).
$^1$H-NMR spectrum (CDCl$_3$/DMF—d$_6$): δ ppm

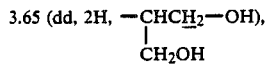
3.65 (dd, 2H, —CHC$\underline{H}_2$—OH), CH$_2$OH

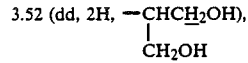
3.52 (dd, 2H, —CHC$\underline{H}_2$OH), CH$_2$OH

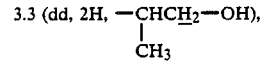
3.3 (dd, 2H, —CHC$\underline{H}_2$—OH), CH$_3$ 1.6 (m, 1H, —C$\underline{H}$(CH$_2$OH)$_2$),

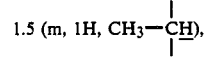
1.5 (m, 1H, CH$_3$—C$\underline{H}$), 1.15–1.37 (m, 8H, —(CH$_2$)$_4$—),
0.83 (d, 3H, CH$_3$—).

REFERENCE EXAMPLE 3

A 100-ml three-necked flask equipped with a liquid-liquid separator for removing producing water, condenser, thermometer and stirrer was charged with 7.06 g (37 millimoles) of a trimethylolheptane and 55% of 1,1,6-trimethylolheptane, 17.2 g (0.15 mole) of caproic acid and 20 ml of benzene. While the mixture was boiled in a nitrogen atmosphere, 0.41 g of p-toulenesulfonic acid was added. The producing water was removed azeotropically with benzene through the liquid-liquid separator. In the course of esterification reaction under the above conditions, the reaction mixture was monitored by gas chromatography. The percent residue of the trimethylolheptane mixture was not more than 1% after 3 minutes of reaction, indicating almost all the trimethylolheptane mixture was esterified within 3 minutes. One hour after the start of reaction, the proportion of the monoesterified trimethylolheptane mixture was not more than 1% of the trimethylolheptane mixture charge. Thus, about 99% of the trimethylolheptane mixture charged was either diesterified or triesterified within 1 hour. After 4 hours of reaction, the proportion of the diesterified trimethylolheptane mixture was not more than 1% of the trimethylolheptane mixture initially charged. Thus, about 99% of the trimethylolheptane mixture charged was triesterfied within 4 hours.

REFERENCE EXAMPLE 4

The esterification procedure of Reference Example 3 was followed except that 5.0 g (37 millimoles) of 1,1,1-trimethylolpropane was used in lieu of 7.06 g (37 millimoles) of the trimethylolheptane mixture. The percent residue of 1,1,1-trimethylolpropane at 6 minutes after initiation of the reaction was not more than 1%, indicating that almost all the 1,1,1-trimethylolpropane had been esterified. At 2 hours after initiation of the reaction, the proportion of monoesterified 1,1,1-trimethylolpropane was not more than 1% of the 1,1,1-trimethylolpropane initially charged or, in other words, about 99% of the 1,1,1-trimethylolpropane charged had been either diesterified or triesterified. At 4 hours after initiation of the reaction, the proportions of 1,1,1-trimethylolpropane diester and triester were 11% and 88% of the 1,1,1-trimethylolpropane initially charged, respectively. At 8 hours after initiation of the reaction, the proportion of 1,1,1-trimethylolpropane diester was not more than 1% or, in other words, about 99% of the 1,1,1-trimethylolpropane initially charged had been triestrified.

EXAMPLES 4–7 AND COMPARATIVE EXAMPLES 1–4

(Production of polyester)

A reaction vessel equipped with a heater, stirrer, fractional distillation column for the separation of producing water and thermometer was charged with 4,945 parts of trimethylolheptane (1,1,7-trimethylolheptane), 8,747 parts of 1,6-hexanediol and 12,728 parts of isophthalic acid, and the mixture was heated to 220° C. over 1 hour. The polycondensation reaction was further continued at 220° C. until the acid value of the resin reached the level of 5.0 mg KOH/g. The reaction mixture was then cooled to 120° C. The thus-obtained resin (polyester resin A) had an acid value of 1 mg KOH/mg and a hydroxyl value of 169 mg KOH/g. The molecular weight calculated based on these data was 1,034.

Using various polyhydric alcohols, the polymerization was carried out in the same manner to give various polyesters. Typical physical characteristics of these resins were measured. They are shown in Table I.

As is evident from Table I, the polyesters obtained by copolymerization with trimethylolheptane have a lower glass transition temperature and a lower viscosity as compared with the polyesters derived from trimethylolpropane.

TABLE 1

| | | Example | | | | Comparative Example | | | |
|---|---|---|---|---|---|---|---|---|---|
| | | 4 | 5 | 6 | 7 | 1 | 2 | 3 | 4 |
| | Resin | A | B | C | D | E | F | G | H |
| Monomer | TMH | 26 | 100 | 26 | 26 | | | | |
| mole | TMP | | | | | 100 | 26 | 26 | 26 |
| ratio | HD | 74 | | 34 | | | 74 | 34 | |
| | ND | | | | 74 | | | | 74 |
| | NPG | | | 40 | | | | 40 | |
| | IPA | 76.6 | 76.6 | 76.6 | 46 | 76.6 | 76.6 | 76.6 | 46 |
| | AD | | | | 31 | | | | 31 |
| Hydroxyl value | | 169 | 290 | 156 | 157 | 377 | 168 | 190 | 165 |
| Acid value | | 1 | 2 | 0.3 | 2 | 7 | 3 | 4 | 2 |
| Molecular weight | | 1034 | 1155 | 1189 | 1089 | 815 | 1058 | 888 | 1039 |
| Viscosity (centipoises) | | 60 | 372 | 439 | 13.4 | ≧1000 | 226 | 851 | 16.1 |
| Glass transition point | | −32° C. | −20° C. | −13° C. | −40° C. | 37° C. | −9° C. | 5° C. | −40° C. |
| Pencil hardness | | F | H | F | HB | 2H | F | H | 2B |
| Tα | | 41 | 63 | 59 | 1 | 88 | 51 | 74 | 5 |

TMH: 1,1,7-Trimethylolheptane
HD: 1,6-Hexanediol
ND: 1:1 Mixture of 1,9-nonanediol and 2-methyl-1,8-octanediol
IPA: Isophthalic acid
TMP: 1,1,1-Trimethylolpropane
NPG: Neopentyl glycol
AD: Adipic acid (Application to polyester paints)

Transparent varnishes were prepared using 70 parts of each polyester resin obtained in the above manner, 30 parts by butyl-etherified melamine resin (product of Dainippon Ink and Chemicals; trademark: Super-Beckamine J820-60) and 0.25 part of p-toluenesulfonic acid.

Each paint was applied to a glass plate, then baked at 140° C. for 60 minutes, and tested for pencil hardness. The paint was also applied to a tinplate, dried, and measured for Tα using a Toyo Sokki model Vibron DDV-II direct-reading dynamic viscoelasticity measuring apparatus (110 Hz). The results thus obtained are also shown in Table I. As is evident from the data shown in the table, the polyesters obtained by copolymerization with trimethylolheptane give a lower Tα, hence better low temperature resistance, than those derived from trimethylolpropane and having the same pencil hardness.

For the paints respectively prepared from the resins A, B, E and F, the rate of curing at 140° C. was determined. The data thus obtained are shown in FIG. 1. It is seen that, with the polyesters according to the invention, the hydroxyl group content decreases rapidly and the cure is complete in a shorter period of time as compared with the polyesters of the comparative examples.

(Application to plyurethane paints)

Figure 2:
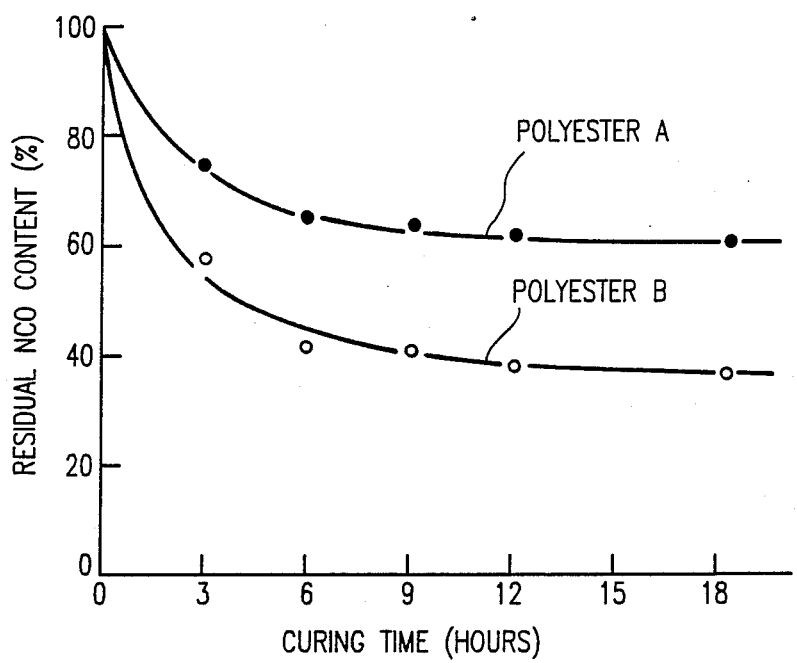
FIG. 2 graphically shows the rates of curing of the polyurethane paints prepared from the resins respectively obtained in Example 5 and Comparative Example 1.

Methyl ethyl ketone (30 parts) was added to 100 parts of the polyester resin B or E. After homogeneous dissolution, a triisocyanate (product of Nippon Polyurethane; trademark: Coronate HL) was added in an amount sufficient to give an NCO/OH ratio of 1/1. The resultant polyurethane paint was used to form a cast film on a sodium chloride sheet. The film was subjected to solid phase reaction at 60° C., and the rate of disappearance of the isocyanato group (NCO) was followed by infrared absorption spectrophotometry. The results thus obtained are shown in FIG. 2.

It is apparent that, with the polyester B, the curing rate is faster as compared with the polyester E.

EXAMPLE 8

(Production of polyester)

The polycondensation procedure of Example 4 was followed except that a trimethylolheptane mixture having the composition given below was used in lieu of 1,1,7-trimethylolheptane. A polyester resin (molecular weight 1,027) having an acid value of 1 mg KOH/g and a hydroxyl value of 170 mg KOH/g was obtained.

1,1,7-Trimethylolheptane 39%
1,2,6-Trimethylolheptane 14%
1,2,7-Trimethylolheptane 26%
1,1,6-Trimethylolheptane 21%

This resin showed a viscosity of 60 poises and a glass transition temperature of −32° C.

(Application to paint)

The polyester resin obtained was used to prepare a paint according to the same formulation as used in Example 4. The paint was applied to a glass plate, baked, and tested for pencil hardness. The pencil hardness was F. The Tα measured in the same manner as in Example 4 was 40° C. The above data indicate that the use of 1,1,7-trimethylolheptane alone for copolymerization and the use of the mixed trimethylolheptane for copolymerization give polyester resins almost comparable in physical characteristics to each other.

EXAMPLE 9

(Production of polyester)

The same reaction vessel as used in Example 4 was charged with 324 parts of dimethyl terephthalate, 324 parts of dimethyl isophthalate, 207 parts of ethylene glycol, 240 parts of 1,9-nonanediol, 104 parts of neopentyl glycol and 0.2 part of titanium propoxide, and the transesterification reaction was carried out at 200° C. for 2 hours. Then, 6 parts of 1,1,7-trimethylolheptane was added, the temperature was raised to 250° C., the reaction was carried out at that temperature for 30 minutes, then the pressure was reduced to 20 mm Hg and maintained at this level for 30 minutes, and the polycondensation reaction was further conducted at 0.3 mm Hg for 60 minutes. The thus-obtained copolyester had a light yellow color and was clear and transparent. Its reduced viscosity was 0.50 dl/g. NMR analysis revealed the following composition: terephthalic acid-/isophthalic acid mole ratio=50/50; ethylene glycol/-neopentyl glycol/1,9-nonanediol/trimethylolheptane mole ratio=39/26/34/1. These mole ratios were almost in agreement with those calculated on the basis of the charge composition.

(Application of paint)

The above polyester was dissolved in a mixed solvent composed of cyclohexanone and Solvesso 150 (50/50 by weight) and the nonvolatile matter content was adjusted to 40%.

A metal painting composition was prepared by kneading a mixture of 100 parts of the above polyester solution, 40 parts of titanium oxide, 10 parts of methyl-etherified methylolmelamine (product of Sumitomo Chemical; trademark: Sumimal M-40S), 0.5 part of a p-toluenesulfonic acid solution (20% benzyl alcohol solution) and 0.2 part of Polyflow S (trademark; product of Kyoeisha Yushi Kagaku Kogyo) in a ball mill for 24 hours.

The paint composition thus obtained was applied, to a thickness of 15–20 μm, to a 0.3 mm thick galvanized sheet (JIS G-3302) pretreated with a zinc phosphate solution. The coat film was baked at 210° C. of 2 minutes. The pencil hardness of the coated steel sheet obtained was at high as 3H, and the flexing resistance was rated at 1T. Thus, the cured coat film was excellent both in hardness and in flexibility.

As the foregoing examples clearly indicate, the polyester resins according to the invention have a low viscosity, shows a high rate of curing reaction with curing agents, and are favorable for use in paint compositions. Coat films obtained by using said resins have good flexibility and low temperature resistance.

EXAMPLE 10

(Production of triacrylate)

A reactor fitted with a stirrer, thermometer, air-blowing pipe and tube for azeotropic water removal was charged with 61 parts of 1,1,7trimethylolheptane, 73 parts of acrylic acid, 80 parts of benzene, 20 parts of cyclohexane, 2 parts of p-toluenesulfonic acid and about 100 ppm of hydroquinone, and the reaction was carried out at 100° C. while air was blown into the mixture. The reaction was monitored by gas chromatography. When it was confirmed that the quantity of byproduct water had almost reached the theoretical quantity, the reaction mixture was neutralized with a 20% aqueous solution of sodium hydroxide, and the organic layer was washed three times with a 20% sodium chloride solution. The organic layer separated was treated in an evaporator at 45° C. for 30 minutes and then, under suction by means of a vacuum pump, at room temperature for 1 hour, for volatile matter elimination therefrom.

The liquid product thus obtained gave the following elemental analysis, infrared absorption spectral and nuclear magnetic resonance spectral data:

| Elemental analysis | | |
|---|---|---|
| | Found | Calculated for ($C_{19}H_{28}O_6$) |
| C (%) | 65.00 | 64.77 |
| H (%) | 7.82 | 7.95 |
| Infrared absorption spectrum | | |
| 1720 $cm^{-1}$ and 1170 $cm^{-1}$ | | ester |
| 1620 $cm^{-1}$ | | terminal vinyl |
| 1460 $cm^{-1}$ | | straight chain methylene |
| Nuclear magnetic resonance spectrum | | |
| 5.5–6.5 ppm | | olefin protons (a) |
| 4.1 ppm | | methylene protons (b) |
| 2.0 ppm | | methine proton (c) |
| 1.1–1.7 ppm | | methylene protons (d) |
| (a):(b):(c):(d) area ratio = 9:6:1:12 | | |

The above results assure that the product obtained was 1,1,7-trimethylolheptane triacrylate.

EXAMPLE 11

(Production of trimethacrylate)

A reactor fitted with a stirrer, thermometer, air-blowing pipe and tube for azeotropic water removal was charged with 61 parts of 1,1,7-trimethylolheptane, 87 parts of methacrylic acid, 80 parts of benzene, 20 parts of cyclohexane, 2 parts of p-toluenesulfonic acid and about 100 ppm of hydroquinone, and the reaction was carried out at 100° C. while air was blown into the mixture. The reaction was monitored by gas chromatography. When it was confirmed that the quantity of byproduct water had almost reached the theoretical quantity, the reaction mixture was neutralized with a 20% aqueous solution of sodium hydroxide, and the organic layer was washed three times with a 20% sodium chloride solution. The organic layer separated was treated in an evaporator at 45° C. for 30 minutes and then, under suction by means of a vacuum pump, at room temperature for 1 hour, for volatile matter removal therefrom.

The thus-obtained liquid product, weighing 123 parts, gave the following elemental ananlysis, infrared absorption spectral and nuclear magnetic resonance spectral data:

| Elemental analysis: | | |
|---|---|---|
| | Found | Calculated for ($C_{22}H_{34}O_6$) |
| C (%) | 72.24 | 70.27 |
| H (%) | 7.86 | 8.11 |
| Infrared absorption spectrum | | |
| 1720 $cm^{-1}$ and 1170 $cm^{-1}$ | | ester |
| 1640 $cm^{-1}$ | | disubstituted olefin |
| 1380 $cm^{-1}$ | | methyl |
| 720 $cm^{-1}$ | | straight chain methylene |
| Nuclear magnetic resonance spectrum | | |
| 5.5, 6.05 ppm | | disubstituted olefin protons (a) |
| 4.1 ppm | | methylene protons (b) |
| 2.0 ppm | | methine proton (c) |
| 1.1–1.7 ppm | | methylene protons (d) |
| 1.8 ppm | | methyl protons (e) |
| (a):(b):(c):(d):(e) area ratio = 6:6:1:12:9 | | |

The above results assure that the product obtained was 1,1,7-trimethylolheptane trimethacrylate.

EXAMPLE 12

(Production of triacrylate)

A reactor fitted with a stirrer, thermometer, air-blowing pipe and tube for azeotropic water removal was charged with 61 parts of 1,1,1-trimethylolheptane, 73 parts of acrylic acid, 80 parts of benzene, 20 parts of cyclohexane, 2 parts of p-toluenesulfonic acid and about 100 ppm of hydroquinone, and the reaction was carried out at 100° C. while air was blown into the mixture. The reaction was monitored by gas chromatography. When it was confirmed that the quantity of byproduct water had almost reached the theoretical quantity, the reaction mixture was neutralized with a 20% aqueous solution of sodium hydroxide and the organic layer was washed with three portions of a 20% sodium chloride solution. The organic layer separated was treated in an evaporator at 45° C. for 30 minutes and further at room temperature under suction by means of a vacuum pump for 1 hour.

The thus-obtained liquid product gave the following elemental analysis, infrared absorption spectral and nuclear magnetic resonance spectral data:

| Elemental analysis: | | |
|---|---|---|
| | Found | Calculated for ($C_{19}H_{28}O_6$) |
| C (%) | 66.90 | 66.67 |
| H (%) | 6.49 | 6.67 |
| Infrared absorption spectrum | | |
| 1720 $cm^{-1}$ and 1170 $cm^{-1}$ | | ester |
| 1620 $cm^{-1}$ | | terminal vinyl |
| 1460 $cm^{-1}$ | | straight chain methylene |
| Nuclear magnetic resonance spectrum | | |
| 5.5–6.5 ppm | | olefin protons (a) |
| 4.1 ppm | | methylene protons (b) |
| 1.2 ppm | | methylene protons (c) |
| 0.8 ppm | | methyl protons (d) |
| (a):(b):(c):(c) area ratio = 9:6:10:3 | | |

(a):(b):(c):(c) area ratio=9:6:10:3

The above results assure that the product obtained was 1,1,1-trimethylolheptane triacrylate.

EXAMPLE 13

(Production of trimethacrylate)

A reactor fitted with a stirrer, thermometer, air-blowing pipe and tube for azeotropic water removal was charged with 61 parts of 1,1,1-trimethylolheptane, 87 parts of methacrylic acid, 80 parts of benzene, 20 parts of cyclohexane, 2 parts of p-toluenesulfonic acid and about 100 ppm of hydroquinone, and the reaction was carried out at 100° C. while air was blown into the mixture. The reaction was conducted for 7 hours under monitoring by gas chromatography. When it was confirmed that the quantity of byproduct water had almost reached the theoretical quantity, the reaction mixture was neutralized with a 20% aqueous solution of sodium hydroxide. The organic layer was further washed with three portions of a 20% sodium chloride solution and then treated in an evaporator at 45° C. for 30 minutes and further at room temperature under reduced pressure under suction by means of a vacuum pump for 1 hour, for volatile matter removal therefrom.

The thus-obtained liquid product gave the following elemental analysis, infrared absorption spectral and nuclear magnetic resonance spectral data:

| Elemental analysis | |
|---|---|
| Found | Calculated for ($C_{22}H_{34}O_6$) |
| C (%) 72.24 | 70.27 |
| H (%) 7.86 | 8.11 |
| Infrared absorption spectrum | |
| 1720 $cm^{-1}$ and 1170 $cm^{-1}$ | ester |
| 1640 $cm^{-1}$ | disubstituted olefin |
| 1380 $cm^{-1}$ | methyl |
| 720 $cm^{-1}$ | straight chain methylene |
| Nuclear magnetic resonance spectrum | |
| 5.5, 6.0 ppm | disubstituted olefin protons (a) |
| 4.1 ppm | methylene protons (b) |
| 1.8 ppm | methyl protons (c) |
| 1.2 ppm | methylene protons (d) |
| 0.8 ppm | methyl protons (e) |
| (a):(b):(c):(d):(e) area ratio = 6:6:9:10:3 | |

(a):(b):(c):(d):(e) area ratio=6:6:9:10:3

The above results assure that the product obtained was 1,1,1-trimethylolheptane trimethacrylate.

EXAMPLE 14

(Confirmation of the reactivity of triacrylate)

To the 1,1,7-trimethylolheptane triacrylate obtained in Example 10 was added 5% of a photoinitiator (manufactured by Ciba Geigy: Irgacure 651) and an appropriate amount of the resulting composition (A) was taken on a rock salt plate and irradiated with ultraviolet light to determine the rate of disappearance of double bonds.

The disappearance of double bonds was assayed by infrared absorption spectrometry based on the decrease in the vinyl group absorption at 1640 $cm^{-1}$ using the carbonyl absorption at 1720 $cm^{-1}$ as an internal reference. For increased accuracy, the assay was carried out in 10 replicates and the mean value was taken.

Figure 3:
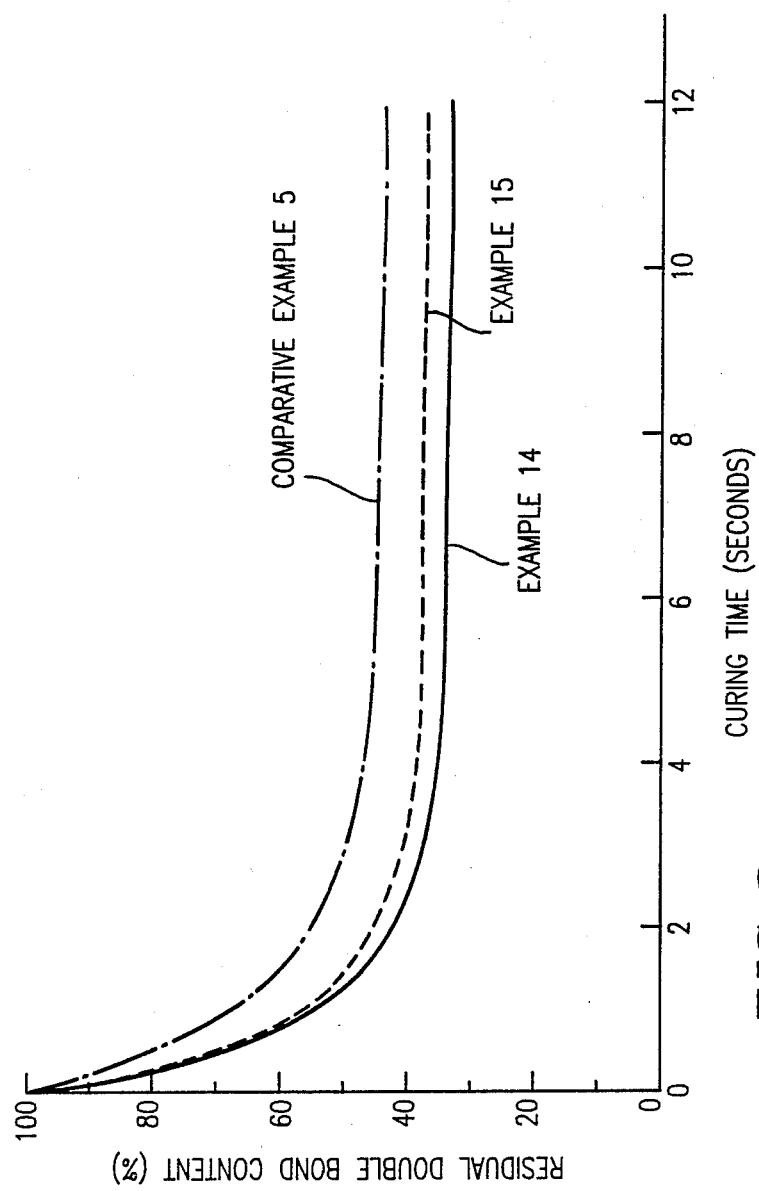
FIG. 3 graphically shows the double bond reactivity of the 1,1,7-trimethylolheptane triacrylate obtained in Example 10, that of the 1,1,1-trimethylolheptane triacrylate obtained in Example 12 and that of trimethylolpropane triacrylate, which is known in the art.

The results are shown in FIG. 3. The initial reaction velocity of this composition (A) was 89%/second and the ultimate reaction rate was 65%.

EXAMPLE 15

(Confirmation of the reactivity of triacrylate)

To the 1,1,1-trimethylolheptane triacrylate obtained in Example 12 was added 5% of a photoinitiator (Ciba Geigy; Irgacure 651) and an appropriate amount of the resulting composition (B) was taken on a rock salt plate and irradiated with ultraviolet light to determine the rate of disappearance of double bonds.

The disappearance of double bonds was assayed by infrared absorption spectrometry based on the decrease in the vinyl group absorption at 1640 $cm^{-1}$ using the carbonyl absorption at 1720 $cm^{-1}$ as an internal reference. For increased accuracy, the assay was carried out in 10 replicates and the mean value was taken.

The results are shown in FIG. 3. The initial reaction velocity of this composition (A) was 87%/second and the ultimate reaction rate was 61%.

COMPARATIVE EXAMPLE 5

The procedure of Example 14 was repeated except that trimethylolpropane triacrylate was used in lieu of the 1,1,7-trimethylolheptane triacrylate used in Example 14 to prepare a composition (C) and the rate of disappearance of double bonds in this composition (C) was determined.

The results are shown in comparison with the results of Examples 14 and 15 in FIG. 3.

The initial reaction velocity of this composition (C) was 54%/second and the ultimate reaction rate was 50%.

EXAMPLE 16

(Confirmation of the reactivity of triacrylate)

Figure 4:
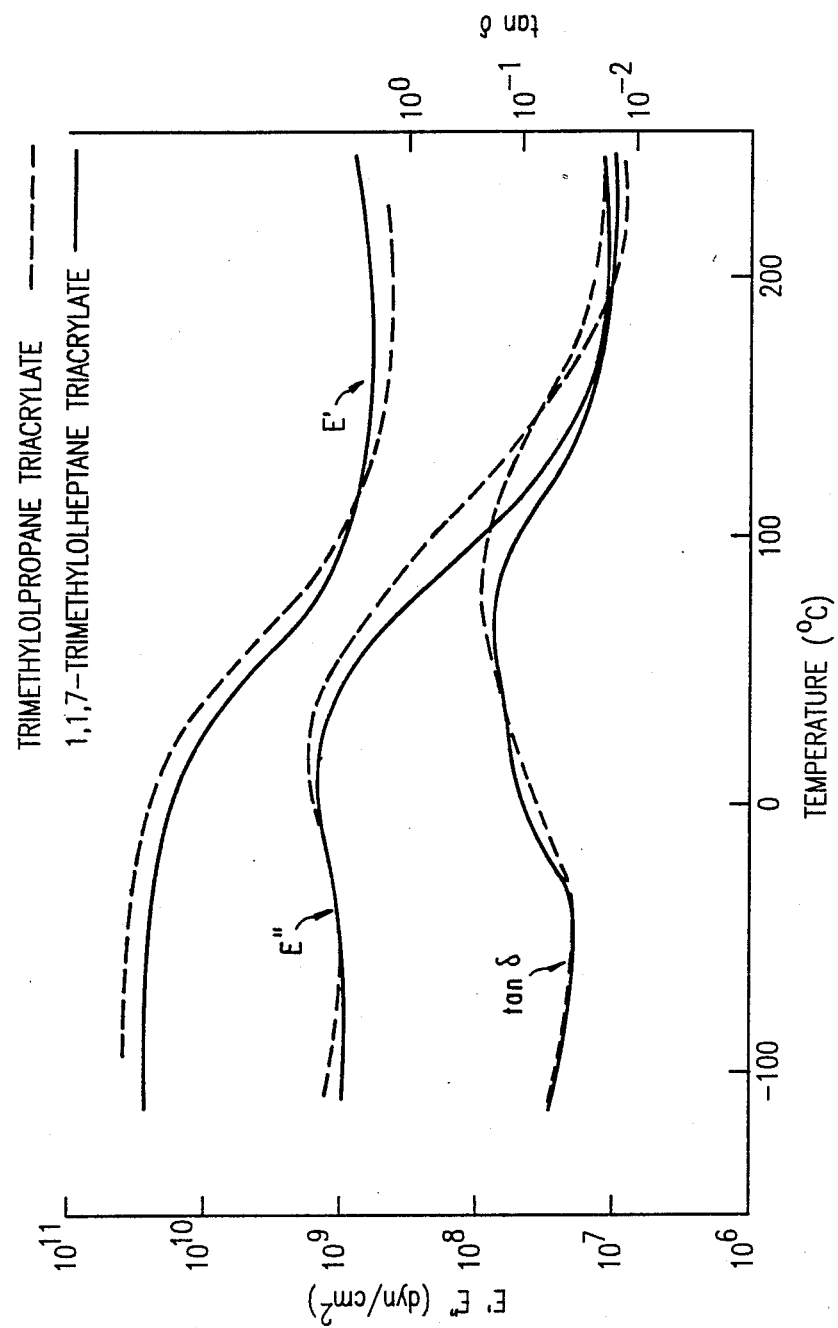
FIG. 4 graphically shows the dynamic viscoelasticity behavior of a curing product from a polyurethane acrylate resin composition containing the 1,1,7-trimethylolheptane triacrylate obtained in Example 10 or the prior art compound trimethylolpropane triacrylate.

To 50 parts of the 1,1,7-trimethylolheptane triacrylate obtained in Example 10 were added 50 parts of a commercial urethane acrylate and 5 parts of a photoinitiator (Ciba Geigy; Irgacure 651) to prepare a polyurethane acrylate resin composition (D). This composition was coated in a thickness of 50 to 100 μm on a polyethylene terephthalate film stuck on a glass sheet and irradiated 5 times with a high-tension mercury-vapor lamp with an output wattage of 80 W/cm under traversing at a speed of 4.5 m/minute. The dynamic viscoelasticity of the cured product was determined in the described manner and evaluated. The results are shown in FIG. 4.

The coating layer became tack-free after the second traversing stroke at a speed of 4.5 m/min. and had been completely cured after the 4th stroke.

EXAMPLE 17

(Confirmation of the reactivity of triacrylate)

Figure 5:
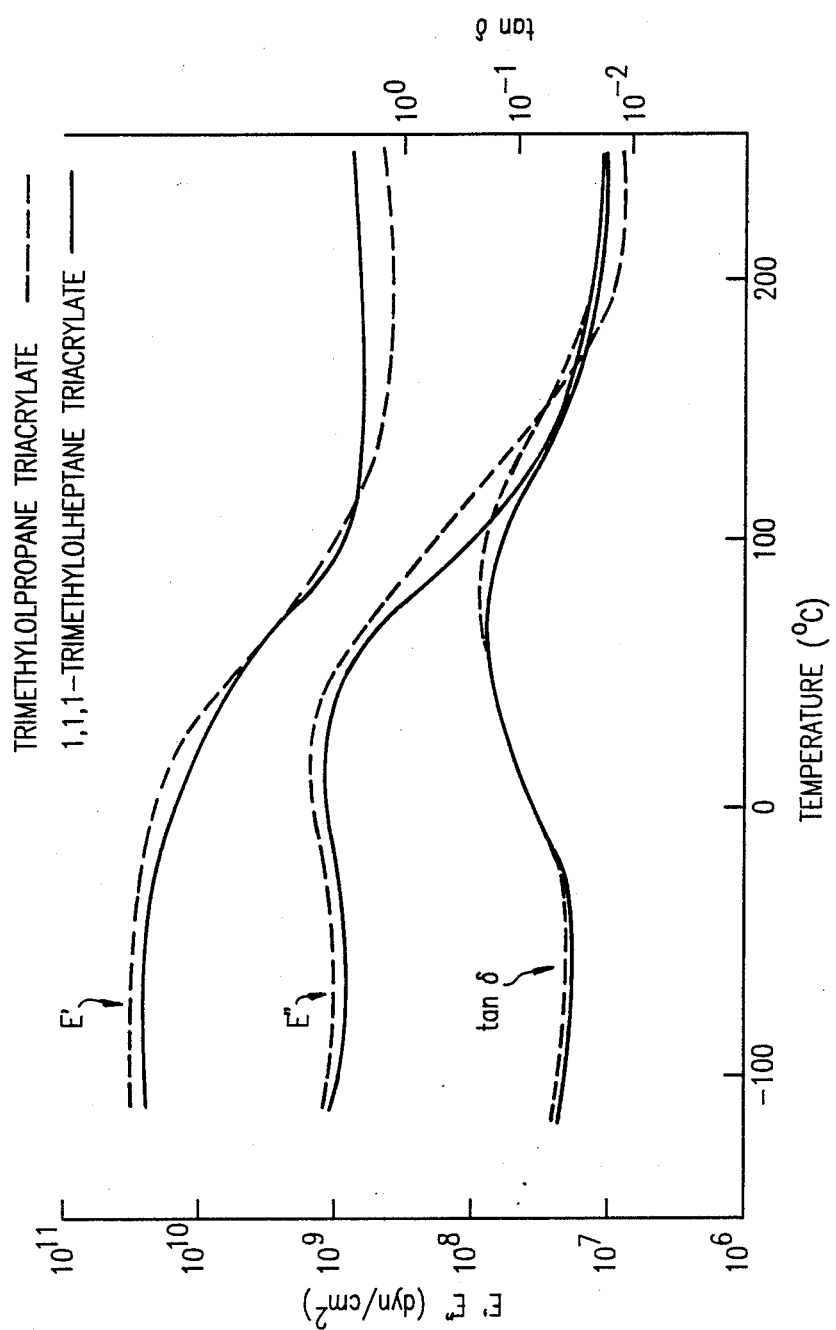
FIG. 5 graphically shows the dynamic viscoelasticity behavior of a curing product from a polyurethane acrylate resin composition containing the 1,1,1-trimethylolheptane triacrylate obtained in Example 12 or the prior art compound trimethylolpropane triacrylate.

To 50 part of the 1,1,1-trimethylolheptane triacrylate obtained in Example 12 were added 50 parts of commercial urethane acrylate and 5 parts of a photoinitiator (Ciba Geigy; Irgacure 651) to prepare a polyurethane acrylate resin composition (E). This composition was coated in a thickness of50 to 100 μm on a polyethylene terephthalate film stuck on a glass sheet and irradiated 5 times with a high-pressure mercury-arc lamp with an output wattage of 80 W/cm under traversing at a speed of 4.5 m/minute. The dynamic viscoelasticity of the cured product was determined in the described manner and evaluated. The results are shown in FIG. 5. The coating layer became tack-free after the second traversing stroke at a speed of 4.5 m/min. and had been completely cured after the 4th stroke.

COMPARATIVE EXAMPLE 6

The procedure of Example 16 was repeated except that trimethylolpropane triacrylate was used in lieu of the 1,1,7-trimethylolheptane triacrylate of Example 10 to prepare a polyurethane acrylate resin composition (F). This composition was coated in a thickness of 50 to 100 μm on a polyethylene terephthalate film stuck on a glass sheet and irradiated 5 times with a high-pressure mercury-arc lamp with an output wattage of 80 W/cm under traversing at a speed of 4.5 m/minute. The dynamic viscoelasticity of the cured product was determined in the described manner and evaluated. The results are shown in FIGS. 4 and 5.

The coating layer became tack-free after the second traversing stroke at a speed of 4.5 m/min. and had been completely cured after the 4th stroke.

COMPARATIVE EXAMPLE 18

(Confirmation of the reactivity of triacrylate)

The procedure of Example 10 was repeated except that in lieu of 1,1,7-trimethylolheptane, a trimethylolheptane, mixture of the following composition was used to prepare a trimethylolheptane triacrylate composition.

| 1,1,7-Trimethylolheptane | 39% |
|---|---|

| | |
|---|---|
| 1,1,6-Trimethylolheptane | 21% |
| 1,2,7-Trimethylolheptane | 26% |
| 1,2,6-Trimethylolheptane | 14% |

The viscosity of the above trimethylolheptane triacrylate was as low as 35 centipoises (at 25° C.).

Then, after addition of a photoinitiator as in Example 14, the rate of disappearance of double bonds was determined. The initial reaction velocity of this rate was 66%.

It will be apparent from the foregoing description that trimethylolheptane tri(meth)acrylates of this invention are low in skin irritability and feature a fast curing speed. Moreover, they offer high diluting effects when used in combination with high molecular weight prepolymers and polymers such as urethane-modified acrylates, polyester acrylates, epoxy acrylates, etc., acting a reactive diluents with good processability and workability as well as excellent curing characteristics. Furthermore, trimethylolheptane tri(meth)acrylates having (meth)acryloyl groups separated by a long methylene chain are particularly satisfactory in diluting effect and extremely high reactivity. Therefore, this invention provides tri(meth)acrylates having characteristics which have never been available before.

We claim:

1. A trimethylolheptane selected from the group consisting of 1,1,7-trimethylolheptane, 1,1,6-trimethylolheptane and 1,6,6-trimethylolheptane.

2. 1,1,7-Trimethylolheptane.

3. A polyester consisting of a polybasic acid component and a polyhydric alcohol component, characterized in that said polyhydric alcohol component is composed of 0.5 mole percent to 100 mole percent of a trimethylolheptane characterized by terminal primary alcohol groups with one hydroxyl group being separated from at least one other hydroxyl group by a carbon chain containing at least 8 carbon atoms, or an ester-forming derivative thereof, and 99.5 mole percent to 0 mole percent of at least one other polyhydric alcohol or an ester-forming derivative thereof, at least 50 percent of the terminal functional groups of said polyester being the hydroxyl group.

4. A polyester as claimed in claim 3, wherein said trimethylolheptane is 1,1,7-trimethylolheptane.

5. A polyester as claimed in claim 3, wherein said trimethylolheptane is a member of the group consisting of 1,1,7-trimethylolheptane, 1,2,7-trimethylolheptane, 1,1,6-trimethylolheptane and 1,2,6-trimethylolheptane or a mixture of two or more of these.

6. A polyester as claimed in claim 3, the main chain of which has at least one fatty acid side chain via ester bonding.

7. A polyester as claimed in claim 6, wherein said fatty acid is a long-chain aliphatic monocarboxylic acid containing 8 to 20 carbon atoms.

8. A polyester as claimed in claim 6, wherein said fatty acid is a member of the group consisting of caprylic acid, capric acid, lauric acid, myristic acid, palmitic acid, stearic acid, oleic acid, ricinolic acid, linolic acid, linolenic acid, eleostearic acid, castor oil, coconut oil, linseed oil, palm oil, safflower oil, soybean oil, tung oil, dehydrated castor oil and tall oil fatty acids, or a mixture of two or more of these.

9. A polyester as claimed in claim 3 or 6, wherein said other polyhydric alcohol is a dihydric alcohol selected from the group consisting of aliphatic diols containing 2 to 12 carbon atoms, polyalkylene glycols, long-chain ester diols and alicyclic or aromatic ring-containing diols containing 8 to 40 carbon atoms, or a mixture of two or more of these.

10. A polyester as claimed in claim 9, wherein said dihydric alcohol is a member of the group consisting of ethylene glycol, propylene glycol, 1,3-butylene glycol, 1,6-hexanediol, neopentyl glycol, 1,9-nonanediol, 2-methyl-1,8-octanediol, 1,10-decanediol, diethylene glycol, triethylene glycol, polyethylene glycol, dipropylene glycol, 2,2-dimethyl-3-hydroxypropyl 2,2-dimethyl-3-hydroxypropionate, hydrogenated bisphenol A and bisphenol A dihydroxypropyl ether, or a mixture of two or more of these.

11. A polyester as claimed in claim 3 wherein said polybasic acid is an aromatic dicarboxylic acid containing 8 to 20 carbon atoms or an aliphatic dicarboxylic acid containing 4 to 40 carbon atoms.

12. A polyester as claimed in claim 3, wherein said polybasic acid is a member of the group consisting of phthalic anhydride, isophthalic acid, terephthalic acid, adipic acid, azelaic acid, sebacic acid, succinic acid, suberic acid, decanedicarboxylic acid, dioleic acid, dilinolenic acid, tetrabromophthalic anhydride, tetrachlorophthalic anhydride, tetrahydrophthalic anhydride, hexahydrophthalic anhydride, chlorendic anhydride, endic anhydride, maleic anhydride, fumaric acid, itaconic acid, dimer acids and succinic anhydride, or a mixture of two or more of these.

13. A polyester as claimed in any of claim 3, wherein the aromatic ring and/or cyclohexane ring content in said polyester is within the range of 1.7 to 3.2 moles per kilogram.

14. A polyester as claimed in any of claim 3, wherein the number average molecular weight of the polyester is within the range of 500 to 30,000.

15. A coating resin composition characterized by containing 60 to 95 percent by weight, on the vehicle basis, of a polyester as claimed in any of claim 3 and 5 to 40 percent by weight, on the same basis, of an aminoplast or a polyisocyanate.

16. A coat film produced by curing of a coating resin composition as claimed in claim 3.

17. A trimethylolheptane triacrylate or trimethyacrylate.

18. A triacrylate or trimethacrylate as claimed in claim 17, which has three terminal methylol acrylate or methacrylate groups and in which one acryloyloxy or methacryloyloxy group is separated from at least one other acryloyloxy or methacryloyloxy group by a carbon chain containing 8 carbon atoms.

19. A triacrylate or trimethacrylate of the general formula $$\begin{array}{c} R_1 \\ | \\ CH_2=C-C-O-(CH_2)_7-CH \\ \phantom{CH_2=C-}\| \\ \phantom{CH_2=C-C-}O \end{array} \Big\langle \begin{array}{c} O \quad R_2 \\ \| \quad | \\ CH_2-O-C-C=CH_2 \\ \\ CH_2-O-C-C=CH_2 \\ \| \quad | \\ O \quad R_3 \end{array} \quad (I)$$

wherein $R_1$, $R_2$ and $R_3$ are the same or different add each is a hydrogen atom or a methyl group.

20. A triacrylate or trimethacrylate as claimed in claim 17, said triacrylate or trimethacrylate being a member of the group consisting of 1,1,1-trimethylolheptane triacrylate, 1,1,1-trimethylolheptane trimethacrylate, 1,1,6-trimethylolheptane triacrylate, 1,1,6trimethylolheptane trimethacrylate, 1,2,7-trimethylolheptane triacrylate, 1,2,7-trimethylolheptane trimethacrylate, 1,6,6-trimethylolheptane triacrylate, 1,6,6-trimethylolheptane trimethacrylate, 1,2,6-trimethylolheptane triacrylate and 1,2,6-trimethylolheptane trimethacrylate.

21. A triacrylate or trimethacrylate composition which is a mixture of at least two compounds selected from the group consisting of 1,1,7-trimethylolheptane triacrylate, 1,1,7-trimethylolheptane trimethacrylate, 1,1,1-trimethylolheptane triacrylate, 1,1,1-trimethylolheptane trimethacrylate, 1,1,6-trimethylolheptane triacrylate, 1,1,6-trimethylolheptane trimethacrylate, 1,2,7-trimethylolheptane triacrylate, 1,2,7-trimethylolheptane trimethacrylate, 1,6,6-trimethylolheptane triacrylate, 1,6,6-trimethylolheptane trimethacrylate, 1,2,6-trimethylolheptane triacrylate and 1,2,6-trimethylolheptane trimethacrylate.

22. A method of producing a trimethylolheptane triacrylate or trimethacrylate which comprises reacting a trimethylolheptane with an acrylic or methacrylic acid or an ester-forming derivative thereof.

23. A method of producing a triacrylate or trimethacrylate of the general formula

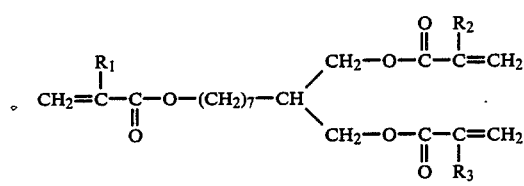

wherein $R_1$, $R_2$ and $R_3$ are the same or different and each is a hydrogen atom or a methyl group, which comprises reacting 1,1,7-trimethylolheptane with an acrylic or methacrylic acid or an ester-forming derivative thereof.

24. A resin composition which contains a trimethylolheptane triacrylate or trimethyacrylate.

25. A resin composition which contains a triacrylate or trimethacrylate of the general formula

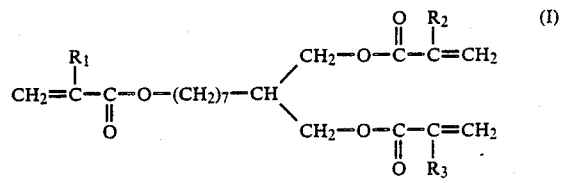

wherein $R_1$, $R_2$ and $R_3$ are the same or different and each is a hydrogen atom or a methyl group.

26. A resin composition as claimed in claim 24 or 25, in which the content of triacrylate or trimethacrylate is within the range of 5 to 99.9 percent by weight on the resin composition basis.

27. A resin composition as claimed in claim 25 which contains a prepolymer.

28. A resin composition as claimed in claim 27, in which the prepolymer is an acrylic oligomer selected from the group consisting of polyester acrylate, polyester methacrylate, polyurethane acrylate, polyurethane methacrylate, epoxy acrylate, epoxy methacrylate, alkyd acrylate, alkyd methacrylate, polyether acrylate, polyether methacrylate, polyol acrylate and polyol methacrylate, or a mixture of two or more of these.

29. A resin composition as claimed in claim 28, which further contains at least one other polymerizable monomer.

30. A resin composition which is composed of 5 to 99.9 percent by weight of trimethylolheptane triacrylate or trimethacrylate, 0.1 to 10 percent by weight of photoinitiator and 0 to 95 percent by weight of radiation-curable prepolymer and/or polymerizable monomer other than said triacrylate or trimethacrylate.

31. A coat film produced by curing of a composition as claimed in any of claim 30.

* * * * *

UNITED STATES PATENT AND TRADEMARK OFFICE
CERTIFICATE OF CORRECTION

PATENT NO. : 4,935,488
DATED : JUNE 19, 1990
INVENTOR(S) : TOSHIHIRO OMATSU ET AL.

It is certified that error appears in the above-identified patent and that said Letters Patent is hereby corrected as shown below:

On the title page item [73]

In the assignee, delete "Kurary" and insert --Kuraray--.

Signed and Sealed this

Twenty-fourth Day of September, 1991

Attest:

HARRY F. MANBECK, JR.

*Attesting Officer*      *Commissioner of Patents and Trademarks*